US008980562B1

(12) United States Patent
Manna

(10) Patent No.: US 8,980,562 B1
(45) Date of Patent: Mar. 17, 2015

(54) METHOD OF SIMULTANEOUS DETECTION AND TYPING OF HUMAN PAPILLOMA VIRUSES

(75) Inventor: Pradip Manna, Overland Park, KS (US)

(73) Assignee: Physicians Reference Laboratory, Overland Park, KS (US)

( * ) Notice: Subject to any disclaimer, the term of this patent is extended or adjusted under 35 U.S.C. 154(b) by 1376 days.

(21) Appl. No.: 12/138,283

(22) Filed: Jun. 12, 2008

Related U.S. Application Data

(60) Provisional application No. 60/943,514, filed on Jun. 12, 2007.

(51) Int. Cl.
*C12Q 1/68* (2006.01)
*C07H 21/04* (2006.01)
*C12Q 1/70* (2006.01)

(52) U.S. Cl.
CPC ............ *C12Q 1/708* (2013.01); *C12Q 2600/16* (2013.01)
USPC ..................... 435/6.12; 536/24.32; 536/24.33

(58) Field of Classification Search
None
See application file for complete search history.

(56) References Cited

U.S. PATENT DOCUMENTS

| | | |
|---|---|---|
| 4,849,331 A | 7/1989 | Lorincz |
| 4,849,332 A | 7/1989 | Lorincz |
| 4,849,334 A | 7/1989 | Lorincz |
| 4,908,306 A | 3/1990 | Lorincz |
| 5,057,411 A | 10/1991 | Lancaster et al. |
| 5,411,857 A | 5/1995 | Beaudenon et al. |
| 5,643,715 A | 7/1997 | Lancaster |
| 5,712,092 A | 1/1998 | Orth et al. |
| 5,952,487 A | 9/1999 | Philipp et al. |
| 5,958,674 A | 9/1999 | Beaudenon et al. |
| 5,981,173 A | 11/1999 | Orth et al. |
| 6,107,086 A | 8/2000 | Cole et al. |

OTHER PUBLICATIONS

Han et al. Simultaneous Amplification and Identification of 25 Human Papillomavirus Types with Templex Technology. Journal of Clinical Microbiology (2006) 44(11): 4157-4162.*

Gheit et al. Development of a Sensitive and Specific Assay Combining Multiplex PCR and DNA Microarray Primer Extension to Detect High-Risk Mucosal Human Papillomavirus Types. Journal of Clinical Microbiology (2006) 44(6): 2025-2031.*

Lowe et al. A computer program for selection of oligonucleotide primers for polymerase chain reactions. Nucleic Acids Research (1990) 18(7): 1757-1761.*

Moberg et al. Real-Time PCR-Based System for Simultaneous Quantification of Human Papillomavirus Types Associated with High Risk of Cervical Cancer. Journal of Clinical Microbiology (2003) 41(7): 3221-3228.*

Rubin et al. Detection and Typing of Human Papillomavirus DNA in Penile Carcinoma. American Journal of Pathology (2001) 159: 1211-1218.*

Lee et al. Seven-Color, Homogeneous Detection of Six PCR Products. BioTechniques (1999) 27: 342-349.*

Bassler et al. Use of a Fluorogenic Probe in a PCR-Based Assay for the Detection of Listeria monocytogenes. Applied and Environmental Microbiology (1995) 61(10): 3724-3728.*

Molenkamp et al. Simultaneous detection of five different DNA targets by real-time Taqman PCR using the Roche LightCycler480: Application in viral molecular diagnostics. Journal of Virological Methods (2007) 141: 205-211.*

Han et al. Journal of Clinical Microbiology 44(11): 4157-4162 (2006).*

Bosch et al., Prevalence of human papillomavirus in cervical cancer: a worldwide perspective, J Nat Cancer Inst, 1995, pp. 796-802, vol. 87, No. 11.

Coulon et al., Molecular cloning and characterization of human papilloma virus DNA derived from a laryngeal papilloma, J Virol, 1982, pp. 393-400, vol. 44, No. 1.

Mayrand et al., Human papillomavirus DNA versus Papanicolaou screening tests for cervical cancer, N Engl J Med, 2007, pp. 1579-1588, vol. 357, No. 16.

Munoz et al., Epidemiologic classification of human papillomavirus types associated with cervical cancer, N Engl J Med, 2003, pp. 518-527, vol. 348, No. 6.

Van Ranst et al., Phylogenetic classification of human papillomaviruses: correlation with clinical manifestations, J Gen Virol, 1992, pp. 2653-2660, vol. 73.

* cited by examiner

*Primary Examiner* — Angela Bertagna
(74) *Attorney, Agent, or Firm* — Hovey Williams LLP

(57) ABSTRACT

The invention relates to a method of detecting HPV and determining HPV type.

20 Claims, 11 Drawing Sheets

FIG. 2A
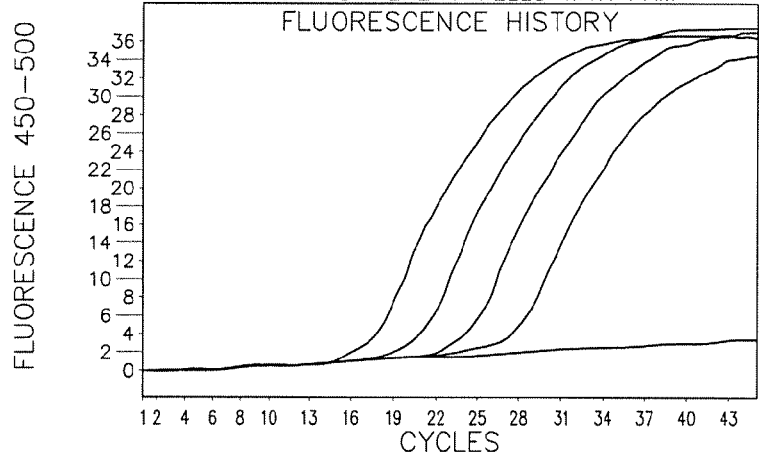
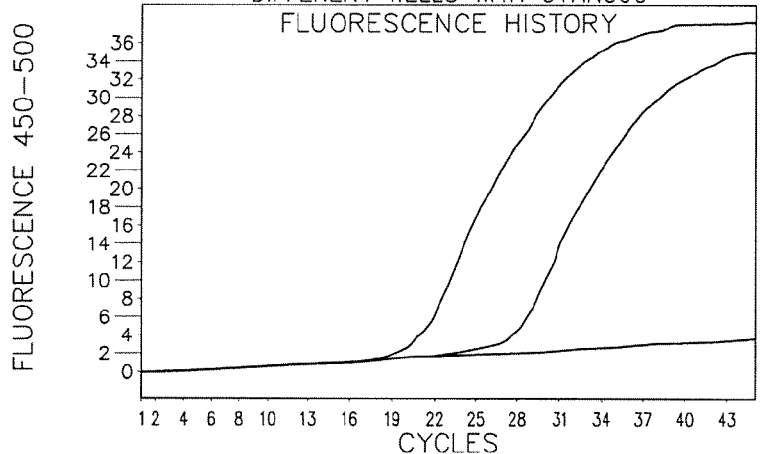
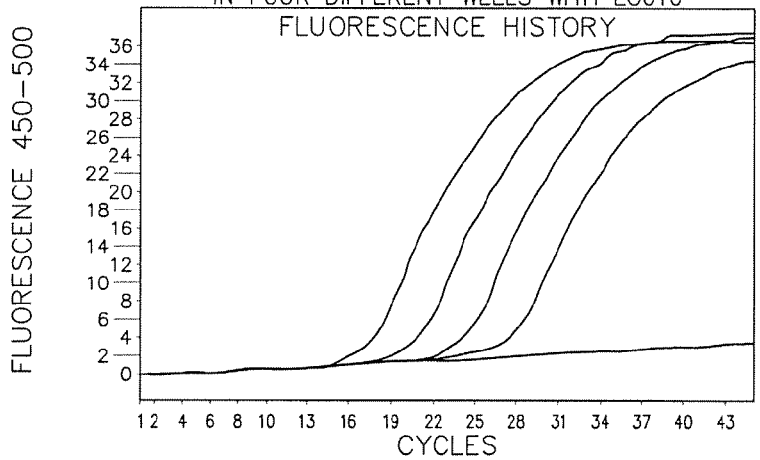

FIG. 2B
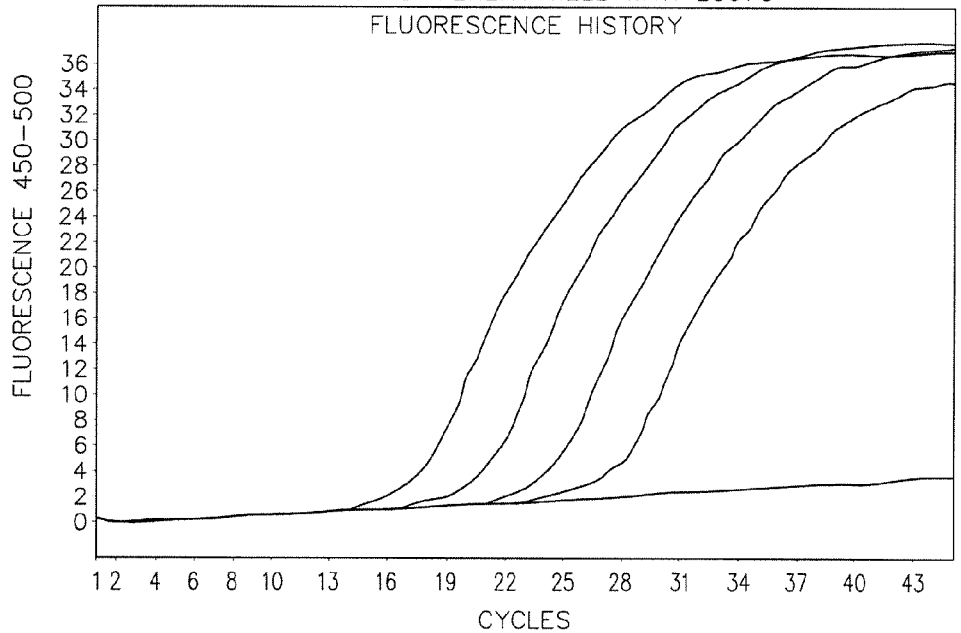
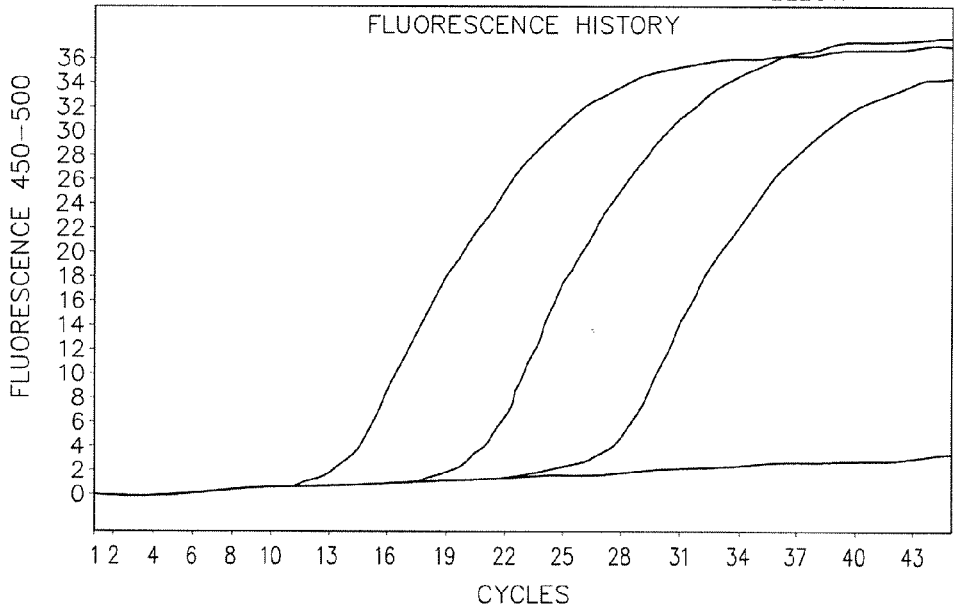

| Sample | B-Mix Cp Value | C-Mix Cp Value |
|--------|----------------|----------------|
| Day 0  | 29.14          | 28.58          |
| Day 2  | 29.18          | 28.63          |
| Day 4  | 29.53          | 28.86          |
| Day 7  | 29.50          | 28.99          |
| Day 9  | 29.67          | 28.94          |
| Day 11 | 29.72          | 29.05          |
| Day 14 | 29.57          | 29.18          |

FIG. 5

| ID number | HPV Type | Multiplex CP Value | Individual CP Value | Multi-type Infections? | Individual Mix |
|---|---|---|---|---|---|
| 375347 | 16 | 22.02/21.06 | 20.78 | Yes-Quadruple | HPV 16 Mix |
| " " | 45 | 34.22 | 32.89 | Yes-Quadruple | HPV 45 Mix |
| " " | 52 | 23.46 | 23.11 | Yes-Quadruple | HPV 52 Mix |
| 427686 | 16 | 33.77/33.41 | 32.92 | Yes-Triple | HPV 16 Mix |
| " " | 56 | 27.19 | 26.86 | Yes-Triple | HPV 56 Mix |
| 421611 | 16 | 32.16/31.74 | 31.21 | Yes-Triple | HPV 16 Mix |
| " " | 18 | 36.58 | 36.31 | Yes-Triple | HPV 18 Mix |
| " " | 52 | 19.08 | 18.79 | Yes-Triple | HPV 52 Mix |
| 398801 | 18 | 33.34 | 32.73 | Yes-Double | HPV 18 Mix |
| " " | 51 | 31.69 | 31.74 | Yes-Double | HPV 51 Mix |
| 402552 | 16 | 21.67/21.31 | 20.93 | Yes-Quadruple | HPV 16 Mix |
| " " | 51 | 22.65 | 22.66 | Yes-Quadruple | HPV 51 Mix |
| " " | 52 | 29.67 | 29.64 | Yes-Quadruple | HPV 52 Mix |
| 405129 | 31 | 31.60 | 31.20 | Yes-Quadruple | HPV 31 Mix |
| " " | 33 | 27.67 | 27.44 | Yes-Quadruple | HPV 33 Mix |
| " " | 18 | 34.53 | 34.23 | Yes-Quadruple | HPV 18 Mix |
| " " | 56 | 30.03 | 30.00 | Yes-Quadruple | HPV 56 Mix |
| 412027 | 51 | 17.27 | 17.03 | Yes-Double | HPV 51 Mix |
| " " | 82 | 30.27 | 29.33 | Yes-Double | HPV 82 Mix |
| 412064 | 16 | 36.43/36.50 | 35.54 | Yes-Triple | HPV 16 Mix |
| " " | 51 | 32.11 | 31.60 | Yes-Triple | HPV 51 Mix |
| 421376 | 16 | 34.36/35.58 | 34.71 | Yes-Double | HPV 16 Mix |
| " " | 73 | 25.40 | 25.05 | Yes-Double | HPV 73 Mix |
| 402530 | 16 | 24.69/25.00 | 24.73 | Yes-Quadruple | HPV 16 Mix |
| " " | 82 | 24.81 | 24.08 | Yes-Quadruple | HPV 82 Mix |

FIG. 6

| Inter-assay | B-Mix Cp | C-Mix Cp |
|---|---|---|
| Mean | 29.25 | 28.80 |
| STDEV | 0.10 | 0.41 |
| CV (%) | 0.36 | 1.45 |

| Intra-Assay | B-Mix Cp | C-Mix Cp |
|---|---|---|
| Mean | 29.35 | 28.80 |
| STDEV | 0.11 | 0.07 |
| CV (%) | 0.36 | 0.24 |

FIG. 7

SEQUENCE LISTING

```
<160> NUMBER OF SEQ ID NOS: 48

<210> SEQ ID NO 1
<211> LENGTH: 29
<212> TYPE: DNA
<213> ORGANISM: Artificial
<220> FEATURE:
<223> OTHER INFORMATION: Synthetic

<400> SEQUENCE: 1
agagacaact gatctctact gttatgagc                                        29

<210> SEQ ID NO 2
<211> LENGTH: 23
<212> TYPE: DNA
<213> ORGANISM: Artificial
<220> FEATURE:
<223> OTHER INFORMATION: Synthetic

<400> SEQUENCE: 2
accgaagcgt agagtcacac ttg                                              23

<210> SEQ ID NO 3
<211> LENGTH: 26
<212> TYPE: DNA
<213> ORGANISM: Artificial
<220> FEATURE:
<223> OTHER INFORMATION: Synthetic
```

```
<220> FEATURE:
<221> NAME/KEY: misc_feature
<222> LOCATION: (1)..(1)
<223> OTHER INFORMATION: Conjugated with a Cyan-500 fluorophore
<220> FEATURE:
<221> NAME/KEY: misc_feature
<222> LOCATION: (26)..(26)
<223> OTHER INFORMATION: Conjugated with Black Berry Quencher

<400> SEQUENCE: 3
aagcagaacc ggacagagcc cattac                                              26

<210> SEQ ID NO 4
<211> LENGTH: 22
<212> TYPE: DNA
<213> ORGANISM: Artificial
<220> FEATURE:
<223> OTHER INFORMATION: Synthetic

<400> SEQUENCE: 4
agcgactcag aggaagaaaa cg                                                  22

<210> SEQ ID NO 5
<211> LENGTH: 26
<212> TYPE: DNA
<213> ORGANISM: Artificial
<220> FEATURE:
<223> OTHER INFORMATION: Synthetic

<400> SEQUENCE: 5
aattctggct tcacacttac aacaca                                              26

<210> SEQ ID NO 6
<211> LENGTH: 35
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Conjugated with a FAM fluorophore
<220> FEATURE:
<221> NAME/KEY: misc_feature
<222> LOCATION: (35)..(35)
<223> OTHER INFORMATION: Conjugated with Black Berry Quencher

<400> SEQUENCE: 6
atagatggag ttaatcatca acatttacca gcccg                                    35

<210> SEQ ID NO 7
<211> LENGTH: 30
<212> TYPE: DNA
<213> ORGANISM: Artificial
<220> FEATURE:
<223> OTHER INFORMATION: Synthetic

<400> SEQUENCE: 7
cgttaccttt tgttgtcagt gtaagtctac                                          30

<210> SEQ ID NO 8
<211> LENGTH: 23
<212> TYPE: DNA
<213> ORGANISM: Artificial
<220> FEATURE:
<223> OTHER INFORMATION: Synthetic

<400> SEQUENCE: 8
```
ccaaatgagc ccattaacag ctc                                           23

<210> SEQ ID NO 9
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Conjugated with a LC-610 fluorophore
<220> FEATURE:
<221> NAME/KEY: misc_feature
<222> LOCATION: (36)..(36)
<223> OTHER INFORMATION: Conjugated with Black Berry Quencher

<400> SEQUENCE: 9
gtttgtgtgt acagagcaca caagtagata ttcgca                             36

<210> SEQ ID NO 10
<211> LENGTH: 20
<212> TYPE: DNA
<213> ORGANISM: Artificial
<220> FEATURE:
<223> OTHER INFORMATION: Synthetic

<400> SEQUENCE: 10
tgaggatgaa ggcttggacc                                               20

<210> SEQ ID NO 11
<211> LENGTH: 27
<212> TYPE: DNA
<213> ORGANISM: Artificial
<220> FEATURE:
<223> OTHER INFORMATION: Synthetic

<400> SEQUENCE: 11
gtactgttga cacataaacg aactgtg                                       27

<210> SEQ ID NO 12
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Conjugated with a FAM fluorophore
<220> FEATURE:
<221> NAME/KEY: misc_feature
<222> LOCATION: (33)..(33)
<223> OTHER INFORMATION: Conjugated with Black Berry Quencher

<400> SEQUENCE: 12
cagctgatta ctacattgta acctgttgtc aca                                33

<210> SEQ ID NO 13
<211> LENGTH: 28
<212> TYPE: DNA
<213> ORGANISM: Artificial
<220> FEATURE:
<223> OTHER INFORMATION: Synthetic

<400> SEQUENCE: 13
cacctccaat tataatattg taacgtcc                                      28

```
<210> SEQ ID NO 14
<211> LENGTH: 18
<212> TYPE: DNA
<213> ORGANISM: Artificial
<220> FEATURE:
<223> OTHER INFORMATION: Synthetic

<400> SEQUENCE: 14
aacagccggg gcacacta                                                 18

<210> SEQ ID NO 15
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Conjugated with a LC-670 fluorophore
<220> FEATURE:
<221> NAME/KEY: misc_feature
<222> LOCATION: (33)..(33)
<223> OTHER INFORMATION: Conjugated with Black Berry Quencher

<400> SEQUENCE: 15
cagagcacac acattgacat acgtaaattg gaa                                33

<210> SEQ ID NO 16
<211> LENGTH: 27
<212> TYPE: DNA
<213> ORGANISM: Artificial
<220> FEATURE:
<223> OTHER INFORMATION: Synthetic

<400> SEQUENCE: 16
tgttcgtgtt gtaagtgtaa caacaca                                       27

<210> SEQ ID NO 17
<211> LENGTH: 26
<212> TYPE: DNA
<213> ORGANISM: Artificial
<220> FEATURE:
<223> OTHER INFORMATION: Synthetic

<400> SEQUENCE: 17
agtccataaa cagctgctgt agttgt                                        26

<210> SEQ ID NO 18
<211> LENGTH: 31
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Conjugated with a LC-610 fluorophore
<220> FEATURE:
<221> NAME/KEY: misc_feature
<222> LOCATION: (31)..(31)
<223> OTHER INFORMATION: Conjugated with Black Berry Quencher

<400> SEQUENCE: 18
ctggtagtag aagcctcacg ggatactctg c                                  31

<210> SEQ ID NO 19
<211> LENGTH: 26
<212> TYPE: DNA
```

```
<213> ORGANISM: Artificial
<220> FEATURE:
<223> OTHER INFORMATION: Synthetic

<400> SEQUENCE: 19
aatgaattag atcctgttga cctgtt                                          26

<210> SEQ ID NO 20
<211> LENGTH: 23
<212> TYPE: DNA
<213> ORGANISM: Artificial
<220> FEATURE:
<223> OTHER INFORMATION: Synthetic

<400> SEQUENCE: 20
gggctggtag ttgtgcatga cta                                             23

<210> SEQ ID NO 21
<211> LENGTH: 29
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Conjugated with a LC-670 flurophore
<220> FEATURE:
<221> NAME/KEY: misc_feature
<222> LOCATION: (29)..(29)
<223> OTHER INFORMATION: Conjugated with Black Berry Quencher

<400> SEQUENCE: 21
tcagaggagg aaaacgatga agcagatgg                                       29

<210> SEQ ID NO 22
<211> LENGTH: 21
<212> TYPE: DNA
<213> ORGANISM: Artificial
<220> FEATURE:
<223> OTHER INFORMATION: Synthetic

<400> SEQUENCE: 22
aattgaagct ccgtgttgca g                                               21

<210> SEQ ID NO 23
<211> LENGTH: 19
<212> TYPE: DNA
<213> ORGANISM: Artificial
<220> FEATURE:
<223> OTHER INFORMATION: Synthetic

<400> SEQUENCE: 23
ccaggcttag ttcgcccat                                                  19

<210> SEQ ID NO 24
<211> LENGTH: 31
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Conjugated with a Yakima-Yellow fluorophore
<220> FEATURE:
<221> NAME/KEY: misc_feature
<222> LOCATION: (31)..(31)
<223> OTHER INFORMATION: Conjugated with Black Berry Quencher
```

-continued

<400> SEQUENCE: 24
tcaagtgtag tacaactggc agtggaaagc a                31

<210> SEQ ID NO 25
<211> LENGTH: 20
<212> TYPE: DNA
<213> ORGANISM: Artificial
<220> FEATURE:
<223> OTHER INFORMATION: Synthetic

<400> SEQUENCE: 25
gcagaacaag ccacaagcaa                             20

<210> SEQ ID NO 26
<211> LENGTH: 22
<212> TYPE: DNA
<213> ORGANISM: Artificial
<220> FEATURE:
<223> OTHER INFORMATION: Synthetic

<400> SEQUENCE: 26
gtaatgtgcc caacagcatt tg                          22

<210> SEQ ID NO 27
<211> LENGTH: 30
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Conjugated with a FAM fluorophore
<220> FEATURE:
<221> NAME/KEY: misc_feature
<222> LOCATION: (30)..(30)
<223> OTHER INFORMATION: Conjugated with Black Berry Quencher

<400> SEQUENCE: 27
cattcatagc actgcgacgg accttcgtac                  30

<210> SEQ ID NO 28
<211> LENGTH: 27
<212> TYPE: DNA
<213> ORGANISM: Artificial
<220> FEATURE:
<223> OTHER INFORMATION: Synthetic

<400> SEQUENCE: 28
cacgtacctt gttgtgagtg taagttt                     27

<210> SEQ ID NO 29
<211> LENGTH: 24
<212> TYPE: DNA
<213> ORGANISM: Artificial
<220> FEATURE:
<223> OTHER INFORMATION: Synthetic

<400> SEQUENCE: 29
gtgacgccat tgcagttagt tact                        24

<210> SEQ ID NO 30
<211> LENGTH: 30
<212> TYPE: DNA
<213> ORGANISM: Artificial
<220> FEATURE:

<223> OTHER INFORMATION: Synthetic
<220> FEATURE:
<221> NAME/KEY: misc_feature
<222> LOCATION: (1)..(1)
<223> OTHER INFORMATION: Conjugated with a LC-610 fluorophore
<220> FEATURE:
<221> NAME/KEY: misc_feature
<222> LOCATION: (30)..(30)
<223> OTHER INFORMATION: Conjugated with Black Berry Quencher

<400> SEQUENCE: 30
acacgcaggt cctctttggt actctgaatg                                       30

<210> SEQ ID NO 31
<211> LENGTH: 22
<212> TYPE: DNA
<213> ORGANISM: Artificial
<220> FEATURE:
<223> OTHER INFORMATION: Synthetic

<400> SEQUENCE: 31
caccacggtt cgtttgtgta tc                                               22

<210> SEQ ID NO 32
<211> LENGTH: 22
<212> TYPE: DNA
<213> ORGANISM: Artificial
<220> FEATURE:
<223> OTHER INFORMATION: Synthetic

<400> SEQUENCE: 32
ttattgctgt gcacagctag gg                                               22

<210> SEQ ID NO 33
<211> LENGTH: 27
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Conjugated with a LC-670 fluorophore
<220> FEATURE:
<221> NAME/KEY: misc_feature
<222> LOCATION: (27)..(27)
<223> OTHER INFORMATION: Conjugated with Black Berry Quencher

<400> SEQUENCE: 33
accctacagc agctgcttat gggcaca                                          27

<210> SEQ ID NO 34
<211> LENGTH: 26
<212> TYPE: DNA
<213> ORGANISM: Artificial
<220> FEATURE:
<223> OTHER INFORMATION: Synthetic

<400> SEQUENCE: 34
cagctagtag tagaaacctc gcaaga                                           26

<210> SEQ ID NO 35
<211> LENGTH: 22
<212> TYPE: DNA
<213> ORGANISM: Artificial
<220> FEATURE:
<223> OTHER INFORMATION: Synthetic

<400> SEQUENCE: 35
ctgcacacaa aggacacaca aa                                          22

<210> SEQ ID NO 36
<211> LENGTH: 29
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Conjugated with a Yakima-Yellow fluorophore
<220> FEATURE:
<221> NAME/KEY: misc_feature
<222> LOCATION: (29)..(29)
<223> OTHER INFORMATION: Conjugated with Black Berry Quencher

<400> SEQUENCE: 36
cgagccttac agcagctgtt tatggacac                                   29

<210> SEQ ID NO 37
<211> LENGTH: 29
<212> TYPE: DNA
<213> ORGANISM: Artificial
<220> FEATURE:
<223> OTHER INFORMATION: Synthetic

<400> SEQUENCE: 37
cagtgtacgt gttgtaagtg taacaacct                                   29

<210> SEQ ID NO 38
<211> LENGTH: 22
<212> TYPE: DNA
<213> ORGANISM: Artificial
<220> FEATURE:
<223> OTHER INFORMATION: Synthetic

<400> SEQUENCE: 38
cacaccacgg acacacaaaa tt                                          22

<210> SEQ ID NO 39
<211> LENGTH: 27
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Conjugated with a FAM fluorophore
<220> FEATURE:
<221> NAME/KEY: misc_feature
<222> LOCATION: (27)..(27)
<223> OTHER INFORMATION: Conjugated with Black Berry Quencher

<400> SEQUENCE: 39
agttctagct tccgcaggtt ctcccgc                                     27

<210> SEQ ID NO 40
<211> LENGTH: 26
<212> TYPE: DNA
<213> ORGANISM: Artificial
<220> FEATURE:
<223> OTHER INFORMATION: Synthetic

<400> SEQUENCE: 40
acaagctgaa cgagagtgtt acagaa                                      26

```
<210> SEQ ID NO 41
<211> LENGTH: 20
<212> TYPE: DNA
<213> ORGANISM: Artificial
<220> FEATURE:
<223> OTHER INFORMATION: Synthetic

<400> SEQUENCE: 41
gtttctggaa cagttggggc                                              20

<210> SEQ ID NO 42
<211> LENGTH: 28
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Conjugated with a LC-610 fluorophore
<220> FEATURE:
<221> NAME/KEY: misc_feature
<222> LOCATION: (28)..(28)
<223> OTHER INFORMATION: Conjugated with Black Berry Quencher

<400> SEQUENCE: 42
cacgaagtgt cagtgcacag tatgccctt                                    28

<210> SEQ ID NO 43
<211> LENGTH: 24
<212> TYPE: DNA
<213> ORGANISM: Artificial
<220> FEATURE:
<223> OTHER INFORMATION: Synthetic

<400> SEQUENCE: 43
aggtgttcga gtgttgtaca gctc                                         24

<210> SEQ ID NO 44
<211> LENGTH: 20
<212> TYPE: DNA
<213> ORGANISM: Artificial
<220> FEATURE:
<223> OTHER INFORMATION: Synthetic

<400> SEQUENCE: 44
ttgccgatgt tagttggtcg                                              20

<210> SEQ ID NO 45
<211> LENGTH: 28
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Conjugated with a LC-670 fluorophore
<220> FEATURE:
<221> NAME/KEY: misc_feature
<222> LOCATION: (28)..(28)
<223> OTHER INFORMATION: Conjugated with Black Berry Quencher

<400> SEQUENCE: 45
tcagcaaatg ttactgggcg acctaagc                                     28

<210> SEQ ID NO 46
<211> LENGTH: 20
```

```
<212> TYPE: DNA
<213> ORGANISM: Artificial
<220> FEATURE:
<223> OTHER INFORMATION: Synthetic

<400> SEQUENCE: 46
cagggctggg cataaaagtc                                              20

<210> SEQ ID NO 47
<211> LENGTH: 25
<212> TYPE: DNA
<213> ORGANISM: Artificial
<220> FEATURE:
<223> OTHER INFORMATION: Synthetic

<400> SEQUENCE: 47
tttgaggttg ctagtgaaca cagtt                                        25

<210> SEQ ID NO 48
<211> LENGTH: 34
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Conjugated with a YAK fluorophore
<220> FEATURE:
<221> NAME/KEY: misc_feature
<222> LOCATION: (34)..(34)
<223> OTHER INFORMATION: Conjugated with Black Berry Quencher

<400> SEQUENCE: 48
cagagccatc tattgcttac atttgcttct gaca                              34
```

METHOD OF SIMULTANEOUS DETECTION AND TYPING OF HUMAN PAPILLOMA VIRUSES

RELATED APPLICATIONS

This Application claims the priority of Provisional Application No. 60/943,514, which is hereby incorporated by reference herein.

INCORPORATION-BY-REFERENCE OF SEQUENCE LISTING IN COMPUTER READABLE FORM

The Sequence Listing, which is a part of the present disclosure, includes a computer readable form file entitled "SNR70000279-0005_Sequence_Listing_ST25.txt" comprising nucleotide and/or amino acid sequences of the present invention submitted via EFS-Web. The subject matter of the Sequence Listing is incorporated herein by reference in its entirety.

TECHNICAL FIELD OF THE INVENTION

The invention relates to a method for detecting Human Papilloma Virus (HPV) in both males and females.

BACKGROUND OF THE INVENTION

Worldwide, cervical cancer is the second most common form of female cancer with incidence of over 500,000 new cases and 300,000 deaths each year. However, if detected early, cervical cancer precursors can be treated effectively. Research worldwide has clearly shown that virtually all cervical cancer is caused by human papillomavirus (HPV) (1-5). In addition, carcinogenic HPV also causes about 200,000 cases of cancer in other sites such as oropharynx, anus, oral cavity, larynx, vulva, and penis worldwide annually. Women persistently infected with certain carcinogenic types are at increased risk of developing severe dysplasia leading to cervical cancer. Cervical cancer prevention programs in both developed and developing nations generally have relied on cytological testing using the Papanicolaou (Pap) smear test (6). Pap smears require that a health care provider obtain a sample of cells from the uterine cervix of each woman screened. Trained technicians then examine the specimen for cellular changes (dysplasia) known to precede the development of cervical cancer. Such screening programs can be expensive, prone to error, and less sensitive (7-10). The direct detection of HPV in cervical specimens offers an alternative or complement to population-based cytological screening. Recent studies have demonstrated that molecular HPV test results are more sensitive than Pap smears in detecting cervical cancer. There are over 100 different HPV types of which only 15 are known as high risk, those typically associated with cervical cancer, whereas three others are known as probable high risk because of their low prevalence rate. Recent studies show that not all HPV types are equally prevalent or carcinogenic (11). For example, the odd ratio or the likelihood of developing cervical cancer with the presence of HPV16 is 434× greater than without HPV16, whereas it is 45× greater in the presence of HPV45 than without HPV45.

Human Papilloma Viruses are small, double-stranded DNA viruses that infect mucosal and cutaneous epithelia through tiny cuts and abrasions that expose cells of the basal layers. Benign diseases such as hand warts, laryngeal warts, verrucas and numerous other skin lesions can be attributed to infection by one of the 100-plus members of the family of HPV. The individual virus types are defined by DNA sequence homology, and the resulting phylogenetic trees (12-13) can also be related to the pathologies induced by specific types.

The cloning of HPV genomes into bacterial plasmid vectors in the early 1980s (14) later led the realization that HPV infection was linked to cervical cancer. The consequent surge in research activity indicated that over 99% of cervical tumors contain HPV DNA, around 65% being positive for one of the two commonest high-risk types, HPV 16 and 18. DNA sequence determination and classification led to the identification of HPV types such as 16, 18, 31, 33, 35, 39, 45, 51, 52, 56, 58, 59, 68, 73 and 82 were termed 'high risk for cancer induction', and 26, 53, and 66 were termed 'probably high risk', while twelve others (6, 11, 40, 42, 43, 44, 54, 61, 70, 72, 81) were grouped together as 'low risk'.

Prompt and accurate diagnosis is the key to effective disease management and contributes significantly to positive outcomes in many aggressive and life threatening illnesses. Early detection of specific etiologic agents will improve patient management and critically reduce morbidity, mortality of patients, and costs. Modern diagnostic possibilities such as real time polymerase chain reaction (PCR) and genetic chips that identify the cause of the disease prior to the symptoms appearing can help to set new standards in early detection and treatment.

The traditional methods for HPV detection, such as morphological and immunological methods, show low sensitivity and specificity, and do not detect each specific HPV genotype present. However, these methods have many disadvantages, such as requiring a great deal of time and labor to perform the test, the risk of using radioactive isotope, low specificity, high false positive/negative rate, and/or inconvenience in the processes of sample management. Therefore, there is a need in the field for a test with greater specificity that can be done with greater speed.

SUMMARY OF THE INVENTION

The present invention fulfills the above described and other needs by providing a novel and robust method for the detection of, and the determination of the type of HPV viruses in both males and females from a wide variety of sample types.

The present invention provides a method for the detection and determination of at least a genotype of HPV present in a biological sample, which comprises the steps of: a) extracting DNA from a biological sample; b) amplifying the DNA obtained in the sample by a PCR method utilizing at least a coupled set of two primers having the sequences depicted in Columns X and Y of Table I; c) detecting and genotyping of HPV DNA present in the sample by determining the amount of at least a particular PCR product in the sample. The sample comprises DNA isolated from cervical specimens including but not limited to Pap and swab. Further types of samples that will function in the invention include urine, peripheral blood, and other tissues. The invention includes the ability to detect and determine HPV types from DNA isolated from both male and females of all mammalian types including but not limited to humans.

In another aspect the method can detect one, two, three, four, five, six, seven, eight, nine, ten or more variants in a single experiment using PCR primers. The use of all PCR machines could be used successfully in the invention, but a particularly advantageous type of PCR instrument is a real time PCR instrument. Real time PCR instrument includes the LightCycler. The real time PCR instrument is capable of detecting 5 or more different wavelengths (450-500 nm, 483-533 nm, 523-568 nm, 558-610 nm, 615-670 nm) and can be used in multiplex for type-specific probe detection.

In another aspect the method for the detection and determination of at least a genotype of HPV present in a biological sample, which comprises the steps of: a) extracting DNA from a biological sample; b) amplifying the DNA obtained in the sample by a PCR method utilizing at least a coupled set of three primers having the sequences depicted in Columns X, Y, and Z of Table I; c) detecting and genotyping of HPV DNA present in the sample by determining the amount of at least a particular PCR product in the sample. The sample comprises DNA isolated from cervical specimens including but not limited to Pap and swab. Further types of samples that will function in the invention include urine, peripheral blood, and other tissues and bodily fluids. The invention includes the ability to detect and determine HPV types from DNA isolated from both male and females of all mammalian types including but not limited to humans.

In another aspect the method can detect one, two, three, four, five, six, seven, eight, nine, ten or more or more HPV variants in a single experiment using PCR primers. The use of a variety of PCR machines can be used successfully in the invention, but a particularly advantageous type of PCR instrument is a real time PCR instrument. Real time PCR instrument includes the LightCycler® (Roche Diagnostics Corporation, Indianapolis, Ind.). The real time PCR instrument capable of detecting up to 5 or more different wavelengths (e.g., 450-500 nm, 483-533 nm, 523-568 nm, 558-610 nm, 615-670 nm) can be used in multiplex for type-specific probe detection.

In another aspect the invention includes a method of detecting HPV 16 using primers and optionally, probe comprising SEQ ID NO: 16F, 16R, and optionally, 16P.

In another aspect the invention includes a method of detecting HPV 18 using primers and optionally, probe comprising SEQ ID NO: 18F, 18R, and optionally, 18P.

In another aspect the invention includes a method of detecting HPV 31 using primers and optionally, probe comprising SEQ ID NO: 31F, 31R, and optionally, 31P.

In another aspect the invention includes a method of detecting HPV 33 using primers and optionally, probe comprising SEQ ID NO: 33F, 33R, and optionally, 33P.

In another aspect the invention includes a method of detecting HPV 35 using primers and optionally, probe comprising SEQ ID NO: 35F, 35R, and optionally, 35P.

In another aspect the invention includes a method of detecting HPV 39 using primers and optionally, probe comprising SEQ ID NO: 39F, 39R, and optionally, 39P.

In another aspect the invention includes a method of detecting HPV 45 using primers and optionally, probe comprising SEQ ID NO: 45F, 45R, and optionally, 45P.

In another aspect the invention includes a method of detecting HPV 51 using primers and optionally, probe comprising SEQ ID NO: 51F, 51R, and optionally, 51P.

In another aspect the invention includes a method of detecting HPV 52 using primers and optionally, probe comprising SEQ ID NO: 52F, 52R, and optionally, 52P.

In another aspect the invention includes a method of detecting HPV 56 using primers and optionally, probe comprising SEQ ID NO: 56F, 56R, and optionally, 56P.

In another aspect the invention includes a method of detecting HPV 58 using primers and optionally, probe comprising SEQ ID NO: 58F, 58R, and optionally, 58P.

In another aspect the invention includes a method of detecting HPV 59 using primers and optionally, probe comprising SEQ ID NO: 59F, 59R, and optionally, 59P.

In another aspect the invention includes a method of detecting HPV 68 using primers and optionally, probe comprising SEQ ID NO: 68F, 68R, and optionally, 68P.

In another aspect the invention includes a method of detecting HPV 73 using primers and optionally, probe comprising SEQ ID NO: 73F, 73R, and optionally, 73P.

In another aspect the invention includes a method of detecting HPV 82 using primers and optionally, probe comprising SEQ ID NO: 82F, 82R, and optionally, 82P.

In another aspect the invention includes a method of detecting beta-globin using primers and optionally, probe comprising SEQ ID NO: BG-F, BG-R, and optionally, BG-P.

In another aspect the invention includes a method of determining the risk of HPV transmission by a male comprising detecting HPV in a male human including testing the peripheral blood, penile swab, urine, and all other bodily fluids.

In another aspect the method for the detection and determination of at least a genotype of HPV present in a biological sample wherein the PCR product is detected by use of gene chip, microarray, hybridization, or microfluidic PCR using the primers and probes herein.

In another aspect the invention includes a method for HPV genotype-specific risk assessment, comprising: a) obtaining confirmation of the presence or absence of at least 5 HPV type-specific variants based on detecting E6-E7 nucleic acid targets in a biological sample, and b) evaluating the carcinogenic characteristics of the HPV variants detected in the biological sample.

In another aspect the method for HPV genotype-specific risk assessment, wherein obtaining confirmation of the presence or absence of at least 5 HPV type-specific variants based on detecting E6-E7 nucleic acid targets in a biological sample is achieved by a) extracting DNA from a biological sample; b) amplifying the DNA obtained in the sample by a PCR method utilizing at least a coupled set of five primers having the sequences depicted in Columns X, Y, and Z of Table I; c) detecting and genotyping of HPV DNA present in the sample by analyzing at least a particular PCR product in the sample.

In another aspect the method for HPV genotype-specific risk assessment can be used for assessment of single and co-infections, assessment of new and old infections, pre-vaccine screening, pre-vaccine and post-vaccine monitoring, assessment of viral load, assessment of disease burden, assessment of dysplasia grade, assessment of treatment selection, and monitoring effectiveness of treatment.

In another aspect the method for HPV genotype-specific risk assessment can be used for assessment of cancers selected from the group consisting of penile, anal, oral cavity, oropharynx, and larynx.

The foregoing problems are solved and a technical advance is achieved by the present invention. Disclosed are methods and compositions to treat medical conditions.

BRIEF DESCRIPTION OF THE DRAWINGS

FIGS. 2A and 2B: Multiplex real time PCR for simultaneous detection and type-specific identification of all 15 high risk HPV including internal control beta-globin. Specific fluorophore attached to HPV type-specific probes are detected when a specific wavelength filter is selected in the multiplex reaction.

FIG. 5: B-mix Cp values and C-mix Cp values measured at Day 0, 2, 4, 7, 9, 11, and 14, used to determine specimen stability.

FIG. 6: Comparison of Cp values for HPV types detected in multiplex reactions and single type-specific reactions.

FIG. 7: B-mix Cp values and C-mix Cp values used to determine inter-assay and intra-assay reproducibility.

DESCRIPTION OF THE INVENTION

Figure 1A:
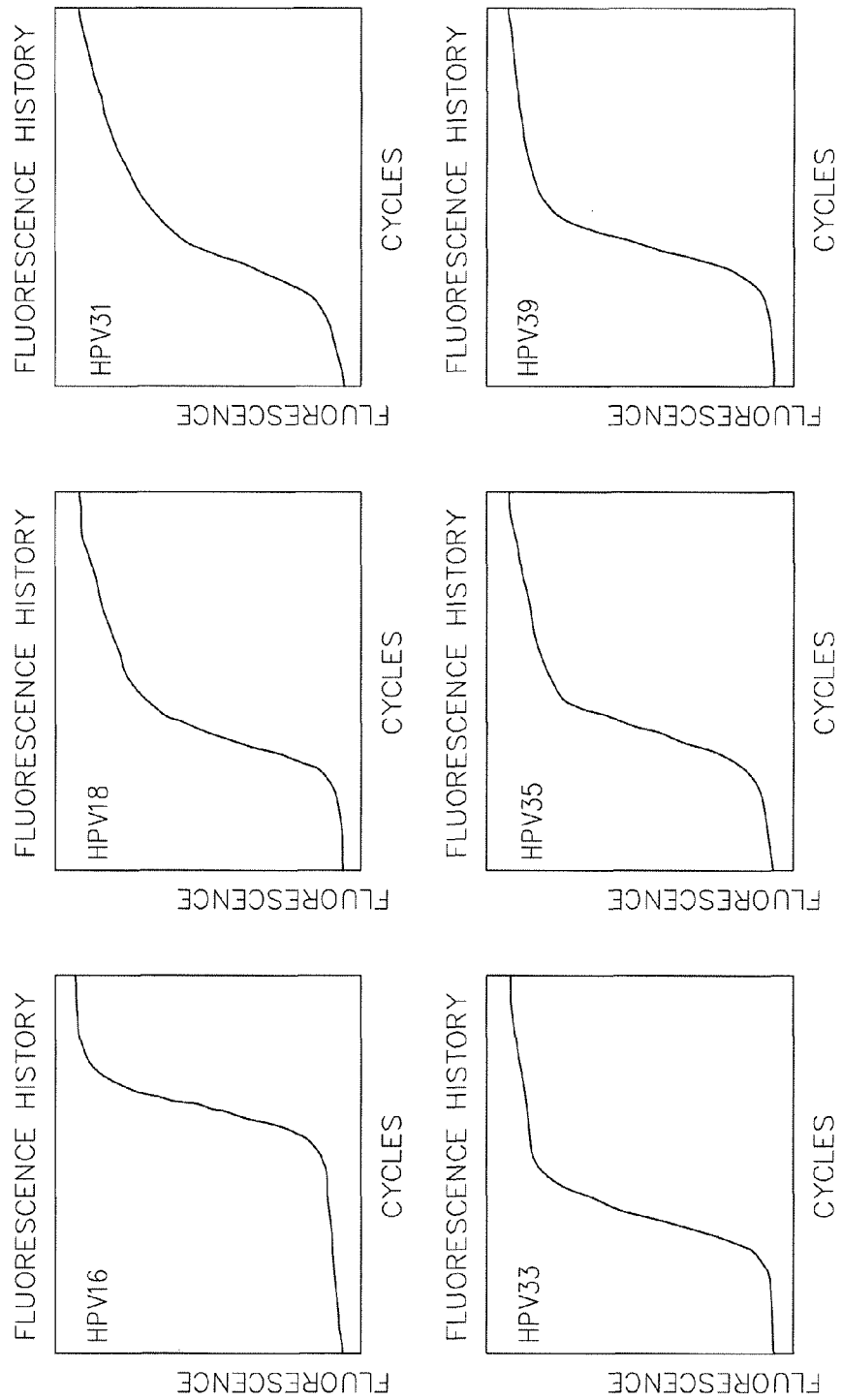
FIGS. 1A, 1B, and 1C: Real time PCR of all 15 high risk HPV including internal control beta-globin in a single reaction for each HPV type. Probes specific for each HPV type are attached with different fluorophores, so that multiplex reaction can be performed to detect many of them together.
Figure 1B:
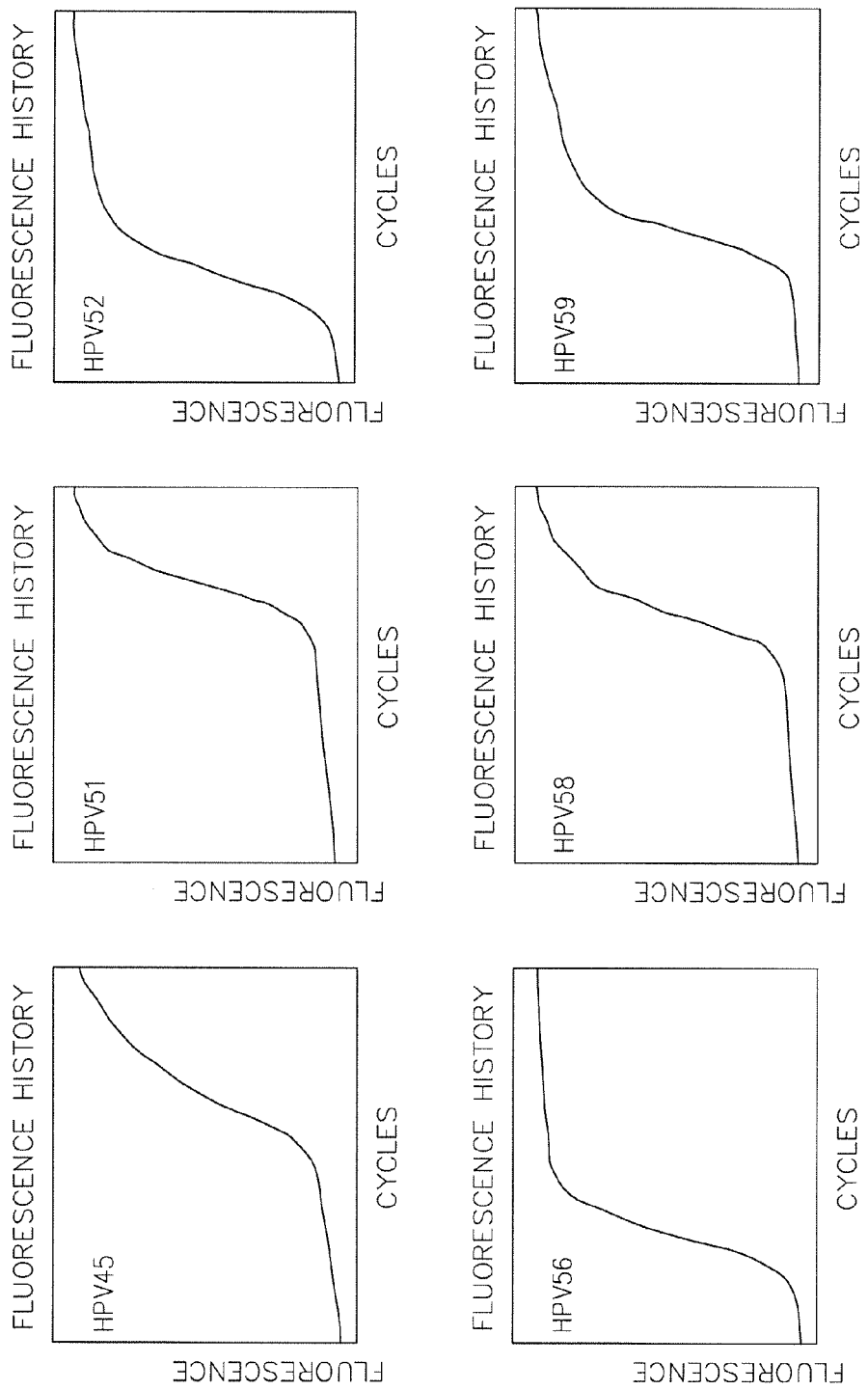
Figure 1C:
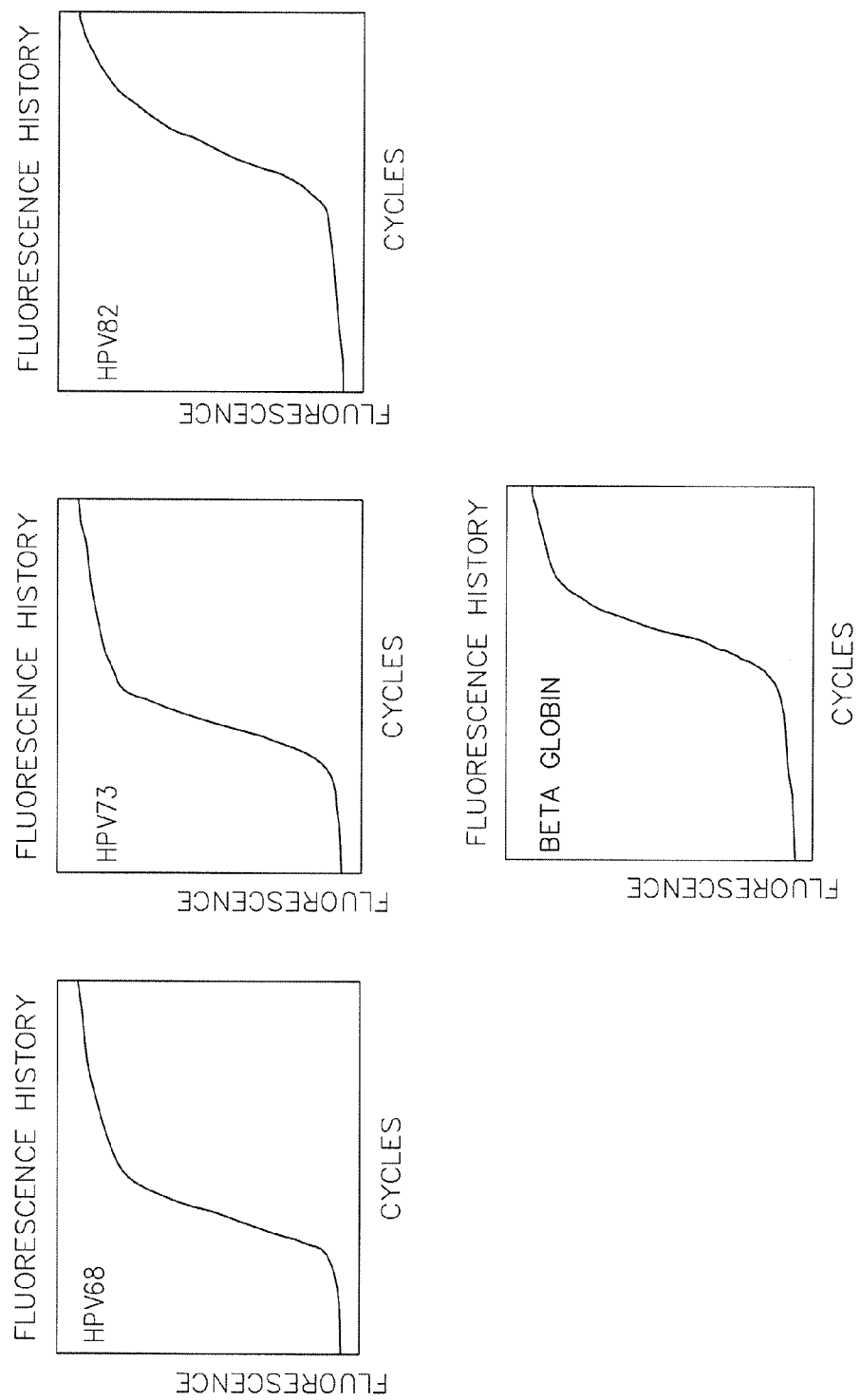

Unless defined otherwise, all technical and scientific terms used have the same meaning as commonly understood by one of ordinary skill in the art to which this invention belongs. Generally, the nomenclature used and the manufacture or laboratory procedures described below are well known and commonly employed in the art. Conventional methods are used for these procedures, such as those provided in the art and various general references. Unless otherwise stated, nucleic acid sequences in the text of this specification are given, when read from left to right, in the 5' to 3' direction. Where a term is provided in the singular, the inventors also contemplate aspects of the invention described by the plural of that term. The nomenclature used and the laboratory procedures described below are those well known and commonly employed in the art. Where there are discrepancies in terms and definitions used in references that are incorporated by reference, the terms used in this application shall have the definitions given. Other technical terms used have their ordinary meaning in the art that they are used, as exemplified by a variety of technical dictionaries. The inventors do not intend to be limited to a mechanism or mode of action. Reference thereto is provided for illustrative purposes only.

DEFINITIONS

"Nucleic acid (sequence)" or "polynucleotide (sequence)" refers to single- or double-stranded DNA (deoxyribonucleic acid) or RNA (ribonucleic acid) of genomic or synthetic origin, i.e., a polymer of deoxyribonucleotide or ribonucleotide bases, respectively, read from the 5' (upstream) end to the 3' (downstream) end. The nucleic acid can represent the sense or complementary (antisense) strand.

"Native" refers to a naturally occurring ("wild-type") nucleic acid sequence.

"Heterologous" sequence refers to a sequence which originates from a foreign source or species or, if from the same source, is modified from its original form. For example, a native promoter could be used to cause the transcription of a heterologous gene from the same or from a different species.

An "isolated" nucleic acid sequence is substantially separated or purified away from other nucleic acid sequences with which the nucleic acid is normally associated in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids.

The term "label" as used herein refers to any atom or molecule that can be used to provide a detectable (preferably quantifiable) effect, and that can be attached to a nucleic acid or protein. Labels include but are not limited to dyes; radiolabels such as radioactive markers (including but not limited to phosphorous, sulfur, iodine, etc.); binding moieties such as biotin; haptens such as digoxygenin; luminogenic, phosphorescent or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry), and the like. A label may be a charged moiety (positive or negative charge) or alternatively, may be charge neutral. Labels can include or consist of nucleic acid or protein sequence, so long as the sequence comprising the label is detectable.

A first nucleic acid or protein sequence displays "substantial identity" to a reference nucleic acid sequence or protein if, when optimally aligned (with appropriate nucleotide or amino acid insertions or deletions totaling less than 20 percent of the reference sequence over the window of comparison) with the other nucleic acid (or its complementary strand) or protein, there is at least about 60% nucleotide sequence equivalence, even better would be 70%, preferably at least about 80% equivalence, more preferably at least about 85% equivalence, and most preferably at least about 90% equivalence over a comparison window of at least 20 nucleotide or amino acid positions, preferably at least 50 nucleotide or amino acid positions, more preferably at least 100 nucleotide or amino acid positions, and most preferably over the entire length of the first nucleic acid or protein. Optimal alignment of sequences for aligning a comparison window may be conducted by the local homology algorithm(s), preferably by computerized implementations of these algorithms (which can be found in, for example, Wisconsin Genetics Software Package Release 7.0, Genetics Computer Group, 575 Science Dr., Madison, Wis.). The reference nucleic acid may be a full-length molecule or a portion of a longer molecule. Alternatively, two nucleic acids have substantial identity if one hybridizes to the other under stringent conditions. Appropriate hybridization conditions can be determined empirically, or can be estimated based, for example, on the relative G+C content of the probe and the number of mismatches between the probe and target sequence, if known. Hybridization conditions can be adjusted as desired by varying, for example, the temperature of hybridizing or the salt concentration (Sambrook et al., *Molecular Cloning: A Laboratory Manual, 2nd Edition*, Cold Spring Harbor Press, 1989).

A "recombinant" nucleic acid or DNA, or RNA molecule is made by an artificial combination of two otherwise separated segments of sequence, e.g., by chemical synthesis or by the manipulation of isolated segments of nucleic acids by genetic engineering techniques. Techniques for nucleic-acid manipulation are well-known (see, e.g., Sambrook et al., *Molecular Cloning: A Laboratory Manual, 2nd Edition*, Cold Spring Harbor Press, 1989). Methods for chemical synthesis of nucleic acids are discussed, for example, in Beaucage and Carruthers, Tetra. Letts. 22:1859-1862, 1981, and Matteucci et al., J. Am. Chem. Soc. 103:3185, 1981. Chemical synthesis of nucleic acids can be performed, for example, on commercial automated oligonucleotide synthesizers.

The terms "recombinant DNA construct", "recombinant vector", "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner.

"Complementary" refers to the natural association of nucleic acid sequences by base-pairing. Complementarity between two single-stranded molecules may be partial, if only some of the nucleic acids pair are complementary; or complete, if all bases pair are complementary. The degree of complementarity affects the efficiency and strength of hybridization and amplification reactions.

"Homology" refers to the level of similarity between nucleic acid or amino acid sequences in terms of nucleotide or amino acid identity or similarity, respectively, i.e., sequence similarity or identity. Homology, homologue, and homologous also refers to the concept of similar functional properties among different nucleic acids or proteins. Homologues include genes that are orthologous and paralogous. Homologues can be determined by using the coding sequence for a gene, disclosed herein or found in appropriate database (such as that at NCBI or others) in one or more of the following ways. For a protein sequence, the sequences should be compared using algorithms (for instance, see section on "identity" and "substantial identity"). For nucleotide sequences the sequence of one DNA molecule can be compared to the sequence of a known or putative homologue in much the same way. Homologues are at least 20% identical, more preferably 30%, more preferably 40%, more preferably 50% identical, more preferably 60%, more preferably 70%, more preferably 80%, more preferably 88%, more preferably 92%, most preferably 95%, across any substantial (25 nucleotide or amino acid, more preferably 50 nucleotide or amino acid, more preferably 100 nucleotide or amino acid, or most preferably the entire length of the shorter sequence) region of the molecule (DNA, RNA, or protein molecule).

Alternatively, two sequences, or DNA or RNA molecules that encode, or can encode, amino acid sequences, are homologous, or homologues, or encode homologous sequences, if the two sequences, or the complement of one or both sequences, hybridize to each other under stringent conditions and exhibit similar function. Thus if one were to determine whether two protein sequences were homologues, one would both do the computer exercises described herein, and create degenerate coding sequences of all possible nucleic acid sequences that could encode the proteins and determine whether they could hybridize under stringent conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to the high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In one preferred embodiment, a nucleic acid of interest in the present invention will specifically hybridize to one or more of the nucleic acid molecules or complements thereof or fragments of either under highly stringent conditions, for example at about 2.0× SSC and about 65° C. The hybridization of the probe to the target DNA molecule can be detected by any number of methods known to those skilled in the art. These can include, but are not limited to, fluorescent tags, radioactive tags, antibody based tags, and chemiluminescent tags.

As used herein, the term "distinct" in reference to signals refers to signals that can be differentiated one from another by spectral properties such as fluorescence emission wavelength, color, absorbance, mass, size, fluorescence polarization properties, charge, etc., or by capability of interaction with another moiety, such as with a chemical reagent, an enzyme, an antibody, etc.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

The term "microarray" refers to an ordered arrangement of hybridizable array elements on a substrate. The term specifically includes polynucleotide microarrays, such as cDNA and oligonucleotide microarrays, and protein arrays. In a particular embodiment, a microarray is an array of thousands of individual gene (DNA) sequences immobilized in a known order on a solid support. RNAs from different tissues are hybridized to the DNA on the chips. An RNA molecule will only bind to the DNA from which it was expressed. As a result, the relative expression of thousands of genes in biological samples The "Complete Care HPV" panel is a real time PCR test that detects all 15 "High Risk" HPVs. Furthermore, this test also detects beta-globin, an internal control to determine the specimen quality, nucleic acid extraction, and PCR reaction inhibition. Applicant has discovered that E6 and E7 region of HPV genome are involved in cancer cell formation and, thus, a preferred target for diagnosing oncogenesis (the E6 and E7 genome sequences are publicly available). Furthermore, for each HPV type there are multiple subtypes/variants. For example, for HPV 16, there are over 40 variants reported and for HPV 18, there are over 18 variants reported. This highly specific and sensitive test consists of 15 individual primer and probe sets that target the conserved E7 region of HPV genome. The test is performed in multiplex real time PCR in 4 wells, Well 1 detects HPV 31, 33, 35, and 59 using a mix of primers and probes mix called "HPV A Mix"; Well 2 detects HPV 16, 18, 51, 56, and 82 using a mix of primers and probes called "HPV B Mix"; Well 3 detects HPV 16, 45, 52, and 73 using a mix of primers and probes called "HPV C Mix"; and Well 4 detects HPV 39, 58, 68, and beta-globin using a mix of primers and probes called "HPV D Mix". The probes, which target individual HPV types, are attached to specific fluorescent dyes in order to identify them within the same well, but with different wavelengths filter channel. Another advantage of this assay is duplicate detection of HPV 16, the major cause of cervical cancer.

Positive controls for the "Complete Care HPV" panel are dilutions of amplified and quantified products of all 15 "High Risk" HPV PCR segments (created by their respective primers) mixed in equal amounts. A $10^2$ stock of positive control specific for each assay mix is used (i.e., segments of HPV 31, 33, 35, and 39 are in the A Mix positive control). In addition to positive controls and a built in internal control, the assay utilizes a no template negative control for each Assay Mix.

The present invention fulfills the above described and other needs by providing a novel and robust method for the detection of, and the determination of the type of HPV viruses in both males and females from a wide variety of sample types.

The present invention provides a method for the detection and determination of at least a genotype of HPV present in a biological sample, which comprises the steps of: a) extracting DNA from a biological sample; b) amplifying the DNA obtained in the sample by a PCR method utilizing at least a coupled set of two primers having the sequences depicted in Columns X and Y of Table I; c) detecting and genotyping of HPV DNA present in the sample by determining the amount of at least a particular PCR product in the sample. The sample comprises DNA isolated from cervical specimens including but not limited to Pap and swab. Further types of samples that will function in the invention include urine, peripheral blood, and other tissues. The invention includes the ability to detect and determine HPV types from DNA isolated from both male and females of all mammalian types including but not limited to humans, and will function with DNA isolated from all sample types.

Extraction of DNA, PCR methods, and isolation of tissues can occur by any known technique including those known to those skilled in the art or found in *Current Protocols in Molecular Biology*, John Wiley & Sons, N.Y. (2005), which is herein incorporated by reference. A variety of all methods of DNA isolation will function in the invention including breaking open cells by grinding or sonication, and removing membrane lipids by adding a detergent; removing cellular and histone proteins bound to the DNA, by adding a protease, by precipitation with sodium or ammonium acetate, or by using a phenol-chloroform extraction step; precipitating DNA in cold ethanol or isopropanol; and other known methods of DNA isolation, further including commercial isolation methods from Qiagen.

In another aspect the method can detect one, two, three, four, five, six, seven, eight, nine, ten, eleven, twelve, thirteen, fourteen or more HPV variants in a single experiment using PCR primers. The use of a variety of PCR machines could be used successfully in the invention, but a particularly advantageous type of PCR instrument is a real time PCR instrument. Real time PCR instruments include the LightCycler. The real time PCR instrument capable of detecting up to 5 or more different wavelengths (e.g., 450-500 nm, 483-533 nm, 523-568 nm, 558-610 nm, 615-670 nm) are used in multiplex for type-specific probe detection. Although specific wavelengths are discussed, any mixture of wavelengths and fluorophores with distinct signals can be used.

The invention includes multiplex PCR using any and all mixtures of primers discussed herein for the detection of all HPV types alone or in any combination.

In molecular biology, real-time polymerase chain reaction, also called quantitative real time polymerase chain reaction (QRT-PCR) or kinetic polymerase chain reaction, is a laboratory technique used to simultaneously quantify and amplify a specific part of a given DNA molecule. It is used to determine whether or not a specific sequence is present in the sample; and if it is present, the number of copies in the sample. It is the real-time version of quantitative polymerase chain reaction (Q-PCR or RQ-PCR), itself a modification of polymerase chain reaction.

The procedure follows the general pattern of polymerase chain reaction, but the DNA is quantified after each round of amplification; this is the "real-time" aspect of it. Two common methods of quantification are the use of fluorescent dyes that intercalate with double-strand DNA, and modified DNA oligonucleotide probes that fluoresce when hybridized with a complementary DNA.

Frequently, real-time polymerase chain reaction is combined with reverse transcription polymerase chain reaction to quantify low abundance messenger RNA (mRNA), enabling a researcher to quantify relative gene expression at a particular time, or in a particular cell or tissue type. Real Time PCR is described in *The Real-Time Polymerase Chain Reaction*, Kubista, M. et. al, *Molecular Aspects of Medicine* 27, 95-125 (2006), Wikpedia, and Applied Biosystems (Foster City, Calif.) Part Number 4371001Revision A, which are all herein incorporated by reference.

Although real-time quantitative polymerase chain reaction is often marketed as RT-PCR, it should not to be confused with reverse transcription polymerase chain reaction, also known as RT-PCR.

In another aspect a method is provided for the detection and determination of at least a genotype of HPV present in a biological sample, and comprises the steps of: a) extracting DNA from a biological sample; b) amplifying the DNA obtained in the sample by a PCR method utilizing at least a coupled set of three primers having the sequences depicted in Columns X, Y, and Z of Table I; c) detecting and genotyping of HPV DNA present in the sample by determining the amount of at least a particular PCR product in the sample. The sample comprises DNA isolated from cervical specimens including but not limited to Pap and swab. Further types of samples that will function in the invention include urine, peripheral blood, and other tissues and bodily fluids, and all bodily fluids and tissues. The invention includes the ability to detect and determine HPV types from DNA isolated from both male and females of all mammalian types including but not limited to humans.

Table I

Shown in Table 1 are primers that can be used in the invention to detect specific HPV. Columns X and Y show paired PCR primers for use in detecting HPV in a sample. Column Z shows a Probe which can be used to quantify the amount of PCR product when used, for example, in a real time PCR, for example, in a LightCycler.

| | Column | | |
|---|---|---|---|
| HPV Type | X Forward Primer | Y Reverse Primer | Z Probe |
| 16 | 16F | 16R | 16P |
| 18 | 18F | 18R | 18P |
| 31 | 31F | 31R | 31P |
| 33 | 33F | 33R | 33P |
| 35 | 35F | 35R | 35P |
| 39 | 39F | 39R | 39P |
| 45 | 45F | 45R | 45P |
| 51 | 51F | 51R | 51P |
| 52 | 52F | 52R | 52P |
| 56 | 56F | 56R | 56P |
| 58 | 58F | 58R | 58P |
| 59 | 59F | 59R | 59P |
| 68 | 68F | 68R | 68P |
| 73 | 73F | 73R | 73P |
| 82 | 82F | 82R | 82P |
| Beta-globin | BG-F | BG-R | BG-P |

In another aspect the method can detect one, two, three, four, five, six, seven, eight, nine, ten, eleven, twelve, thirteen, fourteen or more HPV variants in a single experiment using PCR primers. The use of a variety of PCR machines could be used successfully in the invention, but a particularly advantageous type of PCR instrument is a real time PCR instrument. Real time PCR instrument includes the LightCycler. The real time PCR instrument can be 5 or more different wavelengths (e.g., 450-500 nm, 483-533 nm, 523-568 nm, 558-610 nm, 615-670 nm) are used in multiplex for type-specific probe detection. The invention also includes the use of any and all primers in combination with or without the probe.

In another aspect the invention includes a method of determining the risk of HPV transmission by a male comprising detecting HPV in a male human including testing the peripheral blood, penile swab, urine, and all other bodily fluids.

In another aspect the method for the detection and determination of at least a genotype of HPV present in a biological sample wherein the PCR product is detected by use of gene chip, microarray, hybridization, or microfluidic PCR using the primers and probes herein.

In another aspect the invention includes a method for HPV genotype-specific risk assessment, comprising: a) obtaining confirmation of the presence or absence of at least 5 HPV type-specific variants based on detecting E6-E7 nucleic acid targets in a biological sample, and b) evaluating the carcinogenic characteristics of the HPV variants detected in the biological sample.

In another aspect the method for HPV genotype-specific risk assessment, wherein obtaining confirmation of the presence or absence of at least 5 HPV type-specific variants based on detecting E6-E7 nucleic acid targets in a biological sample is achieved by a) extracting DNA from a biological sample; b) amplifying the DNA obtained in the sample by a PCR method utilizing at least a coupled set of five primers having the sequences depicted in Columns X, Y, and Z of Table I; c) detecting and genotyping of HPV DNA present in the sample by analyzing at least a particular PCR product in the sample.

In another aspect the method for HPV genotype-specific risk assessment can be used for assessment of single and co-infections, assessment of new and old infections, pre-vaccine screening, pre-vaccine and post-vaccine monitoring, assessment of viral load, assessment of disease burden, assessment of dysplasia grade, assessment of treatment selection, and monitoring effectiveness of treatment.

In another aspect the method for HPV genotype-specific risk assessment can be used for assessment of cancers selected from the group consisting of penile, anal, oral cavity, oropharynx, and larynx.

Another embodiment of the invention includes a composition or method according to any of the above mentioned compositions or methods further comprising any combination of any feature defined in any combination of this disclosure. The embodiments discussed herein are only exemplary, and the teaching herein can be expanded by one skilled in the art to encompass many different embodiments.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

EXAMPLES

Example 1

Development and Testing of Primers

DNA Template. Plasmids containing HPV16, -18, -31, -33, -35, -39, -45, -51, -52, -56, -58, -59, -68, -73, and -82 were collected from a variety of sources including from PCR products of detection targets generated by overlapping PCR. Where no target was available, a unique target was determined based on genomic sequence (e.g. 120 bp long). Then two overlapping primers (e.g. 80 bases each that contains 60 unique bases and 20 overlapping bases each) were created and PCR was performed. Then the PCR product from each reaction was mixed together and PCR was performed with a regular primer (e.g. 20 bases) to obtain the full length target.

The copy numbers for individual template was determined by measuring the concentration using PicoGreen dye (Invitrogen, Carlsbad, Calif.).

Real-time PCR. The PCR amplification was performed in a 20-µl volume containing 1× MasterMix (Roche Diagnostics, Indianapolis, Ind.) with a 200 nM concentration of each primer and probe; and variable amount of template DNA. A variable concentration of primers and probes (200 nM-350 nM range), were used in multiplex reaction with the following cycling conditions: pre-incubation at 95° C. for 8 min followed by 45 cycles of 94° C. for 45 sec and 60° C. for 1 min 10 sec, finally the instrument was cooled at 45° C. for 30 sec. A color compensation file was generated with individual positive control present in multiplex reaction along with water control. The color compensation profile was used in the analysis in order to prevent bleed through of one fluorescence wavelength to another wavelength. A LightCycler Real Time PCR machine was used for the PCR reaction, and to collect the data.

Example 2

Determination of HPV Presence and Type in Laboratory Samples

Materials and Methods—Complete Care HPV Panel
a) Preparation of assay mixes and controls:
   a. Assay mixes are made to the required amounts of primers and probes for a given total quantity of assay mix. Concentrations of primers and probes are equal for each HPV type (i.e. 2.5 microM each of HPV 16 forward primer, reverse primer, and probe). Final concentrations of each HPV type are as follows:
      i. A-Mix—2.5 microM of primers and probes for HPV 31, 33, 59 and 5 microM of primers and probes for HPV 35.
      ii. B-Mix—2.5 microM of primers and probes for HPV 18, 51, 56 and 3 microM primers and probes for HPV 16 and 5 microM primers and probes for HPV 82.
      iii. C-Mix—2.5 microM of primers and probes for HPV 16, 52, 73 and 5 microM of primers and probes for HPV 45.
      iv. D-Mix—2.5 microM of primers and probes for HPV 39, 68 and 1.25 microM primers and probes for beta-globin and 5 microM primers and probes for HPV 58.
   b. Positive controls were produced by diluting previously quantitated PCR product corresponding to each individual HPV primer set (and beta-globin). Dilutions were made to a final concentration of 12.5 copies per microL (thus 100 copies per real time reaction when 8 microL are added). PCR product was diluted into TE containing 2 ng/microL MS2 RNA (Roche) to stabilize the low concentration of template DNA. Four individual positive controls were created, each corresponding to the HPV types found in Assay Mixes A, B, C, and D.
b) Preparation of template form clinical specimens:
   a. Thin-prep media (paps):
      i. DNA extraction from clinical specimens collected in ThinPrep media utilize the QIAamp DNA Blood Mini Kit (Qiagen) and its manufacturer suggested protocol with the following modifications.
A. A clinical specimen volume of 1 ml was spun down at 13×1000 rpm for two minutes. Then 800 microL of media was removed to leave a cell pellet and 200 microL of media for further processing.
B. In the elution step, 50 microL of elution buffer AE is added to the Spin Column and allowed to incubate for 5 minutes at room temperature prior to spinning at 13×1000 rpm for 1 minute. Then, a second 50 microL of elution buffer AE is added to the Spin Column and allowed to incubate for 1 minute at room temperature prior to spinning at 13×1000 rpm. This 100 microL is our final patient sample volume.
b. Tissue specimens:
  i. DNA extraction from tissue and paraffin-embedded tissue utilize the QIAamp DNA Mini Kit (Qiagen) and its manufacturer suggested protocol for extractions from tissue with the following modifications.
A. If tissue has been embedded in paraffin, have 6-12 sections cut using common histological techniques. If only slides are available, scrape the tissue off of a minimum of 5 slides. Place material in a 2 ml screw cap tube.
B. If the tissue comes in solution, rinse a piece of the tissue in PBS to remove any fixative, then cut a small piece (a few millimeters). Place in a 2 ml screw cap tube.
C. In the elution step, 25 microL of elution buffer AE is added to the Spin Column and allowed to incubate for 5 minutes at room temperature prior to spinning at 13×1000 rpm for 1 minute. Then, a second 25 microL of elution buffer AE is added to the Spin Column and allowed to incubate for 1 minute at room temperature prior to spinning at 13×1000 rpm. This 50 microL is the final patient sample volume.
c) Reaction set up and real time PCR thermal profiles
a. Reaction mixes:
  i. Reactions are set up in 96-well plates.
  ii. Each individual patient sample well contains 2 microL of Assay Mix A, B, C, or D, 10 microL of Probes Master (Roche), and 8 microL extracted patient sample. Controls contain either 8 microL water or 8 microL of the appropriate Positive Control mix.
  iii. Each patient sample is run in four wells, one with A-Mix, one with B-Mix, one with C-Mix, and one with D-Mix. There are also four negative controls and four positive controls corresponding to each Assay Mix and Positive control mix.
b. Thermal profile:
  i. Pre-incubation—94° C. for 8 minutes
  ii. Amplification:
A. Melting—94° C. for 45 seconds
B. Annealing—60° C. for 70 seconds
  iii. Repeat 1 and 2 for 45 cycles
c. Probe wave-lengths and filters
  A Mix—HPV33-Fam 483-533 nm
  A Mix—HPV59-Yak 523-568 nm
  A Mix—HPV31-610 558-610 nm
  A Mix—HPV35-670 615-670 nm
  B Mix—HPV16-Cyan 450-500 nm
  B Mix—HPV18-Fam 483-533 nm
  B Mix—HPV51-Yak 523-568 nm
  B Mix—HPV56-610 558-610 nm
  B Mix—HPV82-670 615-670 nm
  C Mix—HPV16-Cyan 450-500 nm
  C Mix—HPV52 Fam 483-533 nm
  C Mix—HPV73-610 558-610 nm
  C Mix—HPV45-670 615-670 nm
  D Mix—HPV68-Fam 483-533 nm
  D Mix—HPV39-610 558-610 nm
  D Mix—HPV58-670 615-670 nm
  D Mix—Beta-globin-Yak 523-568 nm
d) Result analysis:
a. Analysis of the results utilizes Absolute Quantitation/$2^{nd}$ Derivative Max within the LightCycler 480 software.
  i. Each individual HPV type is analyzed individually (twice for HPV 16 which is in two mixes). Resulting crossing point (Cp) values for each positive patient sample, beta-globin, and controls are recorded.
  ii. Any unsubstantiated Cp values are recorded and any ambiguous results are brought to the laboratory director.
  iii. All positive controls must have a positive fluorescence signal and all patient samples must have a positive fluorescence signal for beta-globin.
  iv. Positive HPV detections have a Cp value of >36.
This technique was developed and practiced prior to the filing of the patent application. For data employing the primers and probes of Table I in the method described, see FIGS. 1A, 1B, 1C, 2A and 2B.
The below procedural notes further elucidate how this was implemented in a lab setting and provides an example of a detailed protocol that in no way is meant to be limiting, but only exemplary of the method.
Procedural Notes:
Materials and Equipment:
  A. SUPPLIES:
    1. Qiagen QIAamp DNA Mini Kit—Nucleic Acid Extraction Kit
    2. Qiagen QIAamp DNA Blood Mini Kit Nucleic Acid Extraction Kit
    3. 100% Ethanol (NOT denatured alcohol)
    4. Sterile 25 ml serological pipettes
    5. Sterile 1.5 ml disposable transfer pipettes
    6. 2 ml DNase/RNase-free screw cap tubes
    7. 2 ml DNase/RNase-free capless tubes
    8. DNase/RNase-free, aerosol barrier pipette tips
    9. White Tough Spot Labels
    10. Phosphate Buffered Saline
    11. Roche LightCycler 480 Multi-well Plate 96 well plates
    12. Roche LightCycler 480 Sealing Foil
    13. Roche LightCycler 480 Probes Master
    14. Stock HPV Type Specific Primers
    15. Stock HPV Type Specific Probes
    16. Stock Positive Control
    17. Working HPV Assay Mix (i.e. HPV A Mix, HPV B Mix, HPV C Mix, HPV D Mix)
    18. Working Positive Controls
  B. ASSAY MIXES AND CONTROLS:
    1. As needed, HPV Assay Mixes will be made and/or aliquoted and either used directly or frozen for later use.
    2. HPV Assay Mix Preparation Worksheet, aliquot specified primers and probes into amber-colored screw cap tubes.
    3. Labels for the Assay Mixes are to contain the following information:
      a. "HPV A Mix," "HPV B Mix," "HPV C Mix," or "HPV D Mix"
      b. Record Lot Number of primers used.
    4. HPV positive controls are made by mixing together and diluting a known concentration of PCR products to a concentration that will produce $1 \times 10^2$ copies per reaction.

C. STORAGE AND HANDLING RECOMMENDATIONS:

Extraction Kits are stored at 15-25° C. as recommended by the manufacturer. Once re-suspended, Qiagen protease solution used with the QIAamp DNA Blood Mini Kit is stored at 4-6° C. Proteinase K used with the QIAamp DNA Mini Kit is stored at room temperature.

LightCycler 480 Probes Master is stored at −20° C. Once thawed, store at 2-8° C., as recommended by the manufacturer.

HPV primers and probes are stored at either 2-8° C. or −20° C. Once thawed, store at 2-8° C. Keep probes protected from light at all times.

Positive controls are stored at 2-8° C. in R-2.

The working HPV Assay Mixes made in step IV.B. are stored at 2-8° C. Assay mixes are protected from light at all times. Additional aliquots of pre-made HPV Assay Mixes are stored at −20° C.

Working positive controls are stored at 2-8° C.

D. EQUIPMENT
1. Class II biosafety cabinet
2. Plexiglass dead air PCR box
3. Mini centrifuges
4. Eppendorf microtube centrifuge
5. Vortexes
6. Heat blocks
7. Pipette pump
8. P10, P20, P200, P1000 pipettors
9. 2 ml micro tube racks
10. Roche LightCycler 480 System E. CONTROLS
1. Positive Control: Positive controls will be grouped by assay mix to detect problems with any fo the assay mixes during sample runs.
2. Negative Control: A negative or no target control will be set up in 4 wells (one for each assay mix). Negative or no target control reaction includes all the components for positive control except nucleic acid target that is substituted by molecular grade water.
3. Internal Control: Detection of beta-globin, a marker of a human house-keeping gene will serve as both an extraction control and a reaction inhibition control. The HPV D Mix contains primers and probe for amplification and detection of the internal control.

F. PROCEDURE
1. SAMPLE PREPARATION: Specimens are removed from storage and allowed to reach room temperature. Thin prep vials are vortexed just prior to aliquoting specimens for nucleic acid extraction. Master Mix ingredients are calculated and obtained.
2. NUCLEIC ACID EXTRACTION
   a. Protocol A: Thinprep® vials In the biosafety cabinet, specimens are vortexed briefly. Thinprep vials are vortexed immediately prior to aliquotting. 1 ml of each specimen are transferred to appropriately labeled tubes.

Transferred specimens are spun at 13.2 rpm in Eppendorf microcentrifuge for 2 minutes to pellet the cellular material. The upper 800 microL of media from each specimen are aspirated using pipettes and standard length 100-1000 microL tips.

In the biosafety cabinet, 20 microL of protease/proteinase K are added to each 2 ml specimen tube using a pipette and are Vortexed for 5 seconds. If there is a large amount of tissue debris present in the sample, pulse vortex an additional 2×10 seconds. Note: Breaking large tissue clumps helps in digestion by protease for better lysis. However, it may not always be possible to completely dissolve the specimen uniformly.

b. Protocol B: Tissue specimens—These samples are extracted separately from other sample types.

Using the Qiagen QIAamp DNA Mini Kit for extractions from tissue, bring sample to room temperature.

If tissue has been embedded in paraffin, have 6-12 sections cut by the Histology department. If only slides are available, scrape the tissue off of a minimum of 5 slides. Place material in a 2 ml screw cap tube.

Tissue samples are prepared, and Buffer ATL and Proteinase K added before appropriate incubation and vortexing. Tthe sample tubes are then cetrifuged for 30 seconds at 13.2×100 rpm in the Eppendorf microcentrifuge. 200 µl of Buffer AL is added to the sample and mixed by pulse vortexing (5×2 seconds/tube).

The sample is then incubated at 70° C. for 10 minutes and checked occasionally for adequate mixing of the samples.

c. General Extraction:

Samples are buffered and mixed by pulse vortexing (5×2 seconds/per tube). The samples are then incubated and checked for mixing. The sample tubes are centrifuged for 30 seconds at 13.2×100 rpm in the Eppendorf microcentrifuge. 200 µl of 100% ethanol is added to the sample and mixed by pulse vortexing (5×2 seconds/per tube), and centrifuged for 30 seconds at 13.2×1000 rpm in the Eppendorf microcentrifuge. The mixture is carefully applied to a labeled QIAamp Spin Column (in a 2 ml collection tube) without wetting the rim, and centrifuge at 13.2×1000 rpm for 1 minute. The QIAamp Spin Column is placed in a clean 2 ml collection tube and the tube containing the filtrate is discarded. This procedure is repeated one or more time as appropriate.

d. Elution:

The samples are buffered, incubated and spun, and placed in appropriate labeled tubes.

3. REACTION

The reaction mix, including samples and controls is prepared into A-, B-, C- and D-Mix groups as described above and placed into a Lightcycler 480 for amplification and detection. The HPV assay is analyzed using a 5-plex wavelength subset analyzer. The performance data of samples versus controls is interpreted to assess the presence and amount of type-specific HPV. From the type-specific assessment, further assessments are made, depending on patient needs or test purpose, as to risk based on the type-specific profile (including known prevalence and carcinogenic association), single versus co-infections, and new versus old infections. Depending on patient circumstances, this information can be used for pre-vaccine screening and pre- and post-vaccination monitoring. The type-specific profile is highly sensitive and specific, and can be used to assess disease burden, dysplasia grade, and to evaluate the effectiveness of, and further course of treatment.

Probes Used in the Instant Invention Include (Fluorophores are Representative and can be Modified):

```
16F; AGAGACAACTGATCTCTACTGTTATGAGC                                    (SEQ ID NO: 1)
16R; ACC GAA GCG TAG AGT CAC ACT TG                                   (SEQ ID NO: 2)
16P; Cyan 500-AAGCAGAACCGGACAGAGCCCATTAC-BBQ (Black Berry Quencher)   (SEQ ID NO: 3)
18F; AGCGACTCAGAGGAAGAAAACG                                           (SEQ ID NO: 4)
18R; AAT TCT GGC TTC ACA CTT ACA ACA CA                               (SEQ ID NO: 5)
18P; Fam-ATAGATGGAGTTAATCATCAACATTTACCAGCCCG-BBQ                      (SEQ ID NO: 6)
31F; CGTTACCTTTTGTTGTCAGTGTAAGTCTAC                                   (SEQ ID NO: 7)
31R; CCAAATGAGCCCATTAACAGCTC                                          (SEQ ID NO: 8)
31P; LC 610-GTTTGTGTGTACAGAGCACACAAGTAGATATTCGCA-BBQ                  (SEQ ID NO: 9)
33F; TGAGGATGAAGGCTTGGACC                                             (SEQ ID NO: 10)
33R; GTACTGTTGACACATAAACGAACTGTG                                      (SEQ ID NO: 11)
33P; Fam-CAGCTGATTACTACATTGTAACCTGTTGTCACA-BBQ                        (SEQ ID NO: 12)
35F; CACCTCCAATTATAATATTGTAACGTCC                                     (SEQ ID NO: 13)
35R; AAC AGC CGG GGC ACA CTA                                          (SEQ ID NO: 14)
35P; LC 670-CAGAGCACACACATTGACATACGTAAATTGGAA-BBQ                     (SEQ ID NO: 15)
39F; TGTTCGTGTTGTAAGTGTAACAACACA                                      (SEQ ID NO: 16)
39R; AGT CCA TAA ACA GCT GCT GTA GTT GT                               (SEQ ID NO: 17)
39P; LC 610-CTGGTAGTAGAAGCCTCACGGGATACTCTGC-BBQ                       (SEQ ID NO: 18)
45F; AAT GAA TTA GAT CCT GTT GAC CTG TT                               (SEQ ID NO: 19)
45R; GGG CTG GTA GTT GTG CAT GAC TA                                   (SEQ ID NO: 20)
45P; LC 670-TCAGAGGAGGAAAACGATGAAGCAGATGG-BBQ                         (SEQ ID NO: 21)
51F; AATTGAAGCTCCGTGTTGCAG                                            (SEQ ID NO: 22)
51R; CCA GGC TTA GTT CGC CCA T                                        (SEQ ID NO: 23)
51P; Yakima Yellow-TCAAGTGTAGTACAACTGGCAGTGGAAAGCA-BBQ                (SEQ ID NO: 24)
52F; GCAGAACAAGCCACAAGCAA                                             (SEQ ID NO: 25)
52R; GTA ATG TGC CCA ACA GCA TTT GV                                   (SEQ ID NO: 26)
52P; Fam-CATTCATAGCACTGCGACGGACCTTCGTAC-BBQ                           (SEQ ID NO: 27)
56F; CACGTACCTTGTTGTGAGTGTAAGTTT                                      (SEQ ID NO: 28)
56R; GTGACGCCATTGCAGTTAGTTACT                                         (SEQ ID NO: 29)
56P; LC 610-ACACGCAGGTCCTCTTTGGTACTCTGAATG-BBQ                        (SEQ ID NO: 30)
58F; CACCACGGTTCGTTTGTGTATC                                           (SEQ ID NO: 31)
58R; TTATTGCTGTGCACAGCTAGGG                                           (SEQ ID NO: 32)
58P; LC 670-ACCCTACAGCAGCTGCTTATGGGCACA-BBQ                           (SEQ ID NO: 33)
59F; CAGCTAGTAGTAGAAACCTCGCAAGA                                       (SEQ ID NO: 34)
59R; CTG CAC ACA AAG GAC ACA CAA A                                    (SEQ ID NO: 35)
59P; Yakima Yellow-CGAGCCTTACAGCAGCTGTTTATGGACAC-BBQ                  (SEQ ID NO: 36)
68F; CAGTGTACGTGTTGTAAGTGTAACAACCT                                    (SEQ ID NO: 37)
68R; CACACCACGGACACACAAAATT                                           (SEQ ID NO: 38)
68P; Fam-AGTTCTAGCTTCCGCAGGTTCTCCCGC-BBQ                              (SEQ ID NO: 39)
```

```
                                                              -continued
73F; ACAAGCTGAACGAGAGTGTTACAGAA                                                      (SEQ ID NO: 40)

73R; GTT TCT GGA ACA GTT GGG GC                                                      (SEQ ID NO: 41)

73P; LC 610-CACGAAGTGTCAGTGCACAGTATGCCTT-BBQ                                         (SEQ ID NO: 42)

82F; AGGTGTTCGAGTGTTGTACAGCTC                                                        (SEQ ID NO: 43)

82R; TTGCCGATGTTAGTTGGTCG                                                            (SEQ ID NO: 44)

82P; LC 670-TCAGCAAATGTTACTGGGCGACCTAAGC-BBQ                                         (SEQ ID NO: 45)

Beta-globin;
BG-F; CAGGGCTGGGCATAAAAGTC                                                           (SEQ ID NO: 46)

BG-R; TTT GAG GTT GCT AGT GAA CAC AGT T                                              (SEQ ID NO: 47)

BG-P; YAK-CAgAgCCATCTATTgCTTACATTTgCTTCTgACA--BBQ                                    (SEQ ID NO: 48)
```

Example 3

Dynamic Range of Detection

This example illustrates the dynamic range of detection of HPV for a method of HPV detection of the present teachings and establishment of a standard curve for HPV detection.

Figure 3:
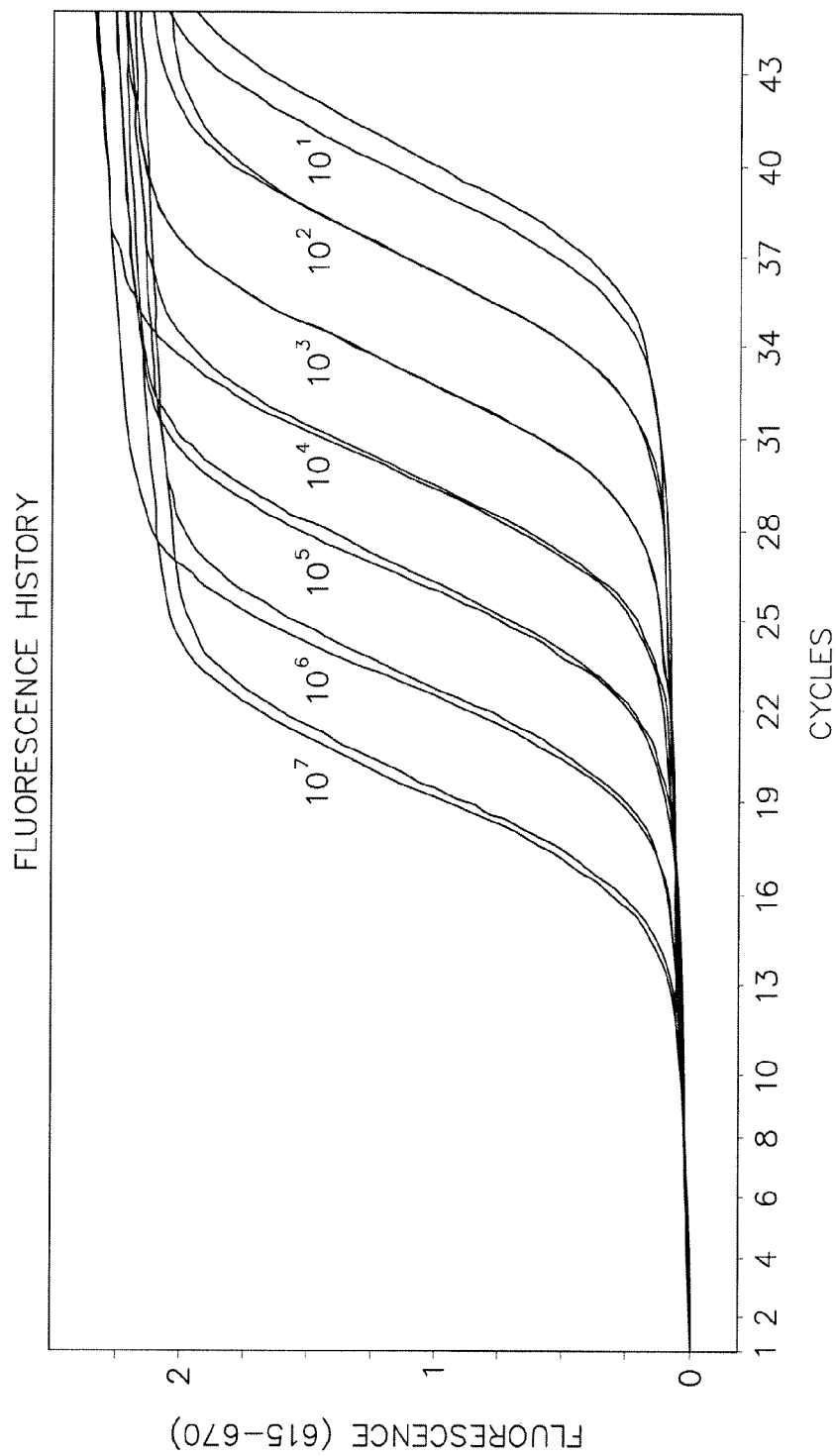
FIG. 3: Multiplex real time PCR dynamic range of detection standard curves.

In this example, standard curves, as shown in FIG. 3, for measuring HPV quantity were determined for 10-fold serial dilutions over a $10^7$-$10^1$ gene copy range, of an HPV sample of known initial concentration. The samples were subjected to real time PCR amplification of a target sequence, and the quantity of amplified DNA was measured using a PicoGreen (Molecular Probes) assay. The gene copy number was then calculated using the length and mass of the amplified DNA. For these calculations, the target gene was presumed present in one copy per HPV genome. The results showed that the assay was sensitive to 10 HPV genomic equivalents per reaction at 40 PCR cycles.

Example 4

Detection of Multiple Hpv Types

This example demonstrates detection of multiple HPV types in a sample and equal efficiency of detection for different HPV types in a sample.

Figure 4:
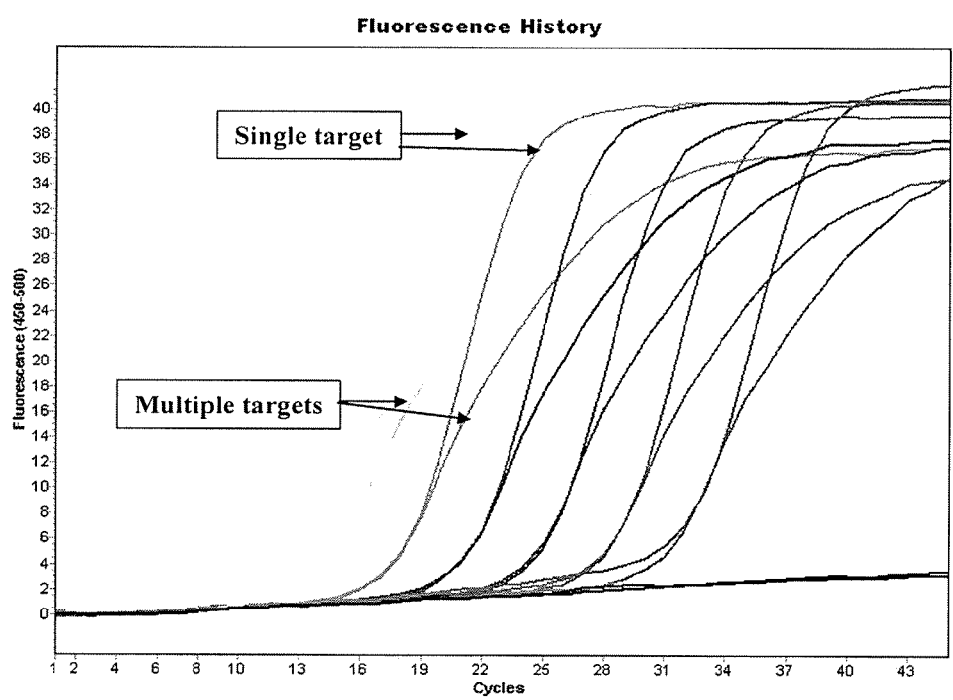
FIG. 4: Real time PCR detection of multiple HPV types in single and multiplex format.

In these experiments, known concentrations of the amplified products from 15 HPV types (HPV16, -18, -31, -33, -35, -39, -45, -51,-52, -56, -58, -59, -68, -73, and -82) were mixed together, serially diluted to obtain $10^1$ to $10^7$ copies/µl for each HPV type, and detected by the method of HPV detection of the present teachings as described in Example 2. The results, as shown in FIG. 4, indicate that the detection efficiencies were not affected by the presence of multiple HPV types at different levels. The threshold Cp values remained the same whether detected in single or in multiplex format. For the multiplex reactions, the lower levels of fluorescence amplitude was due to the use of lower levels of probe concentration optimized for multiplex reaction as compared to single reaction.

Example 5

Specimen Stability

This example demonstrates specimen stability.

In these experiments, a BBI control specimen (BBI Diagnostics, West Bridgewater, Mass.) comprising genomic and HPV 16 DNA was placed on the laboratory bench in ambient temperature. A 200 µL sample of nucleic acid was extracted from the specimen every other day for two weeks. The cross-over point (Cp) values of HPV 16 and a beta-globin internal control were recorded and compared to determine if the specimen integrity had been compromised. No sample or target degradation was detected for the two-week test period, as shown in FIG. 5.

Example 6

Blinded Validation of Method of Hpv Detection

This example demonstrates blinded validation of a method of HPV detection of the present teachings for type-specific identification performance characteristics.

In these experiments, nucleic acid of 15 HPV types (e.g., (HPV16, -18, -31, -33, -35, -39, -45, -51,-52, -56, -58, -59, -68, -73, and -82) was extracted from a library of HPV stock (ATCC and Toshihiko Matsukura, Japan). These nucleic acids were tested by the real time PCR amplification assay described herein, either singly or in combination.

Samples were prepared and coded by one person and tested in blinded manner by another person using the method of HPV detection of the present teachings, as described in Example 2, in single and multiplex reactions, after which the results were compared. All HPV types were tested at least in duplicates. All 15 HPV types were detected in single and multiplex reactions.

Example 7

Detection of Co-Infections

This example illustrates that detection of co-infections within a single reaction mix in a single well are not a result of signal bleed-through in multiplex reaction.

In these experiments, a method of HPV detection of the present teachings was performed in multiplex reaction on samples having single infections with one HPV type and co-infections with multiple HPV types. Of the samples tested in the multiplex reaction, 10 specimens were detected to have co-infections with multiple HPV types. Cp values for the 10 specimens were recorded. Then single type-specific reactions were performed for 10 specimens that were detected to have co-infections with multiple HPV types. The results, as shown in FIG. 6, showed accurate identification of all HPV types in the multiplex reaction. (e.g., HPV Mix A, B, C, or D).

Example 8

Inter- and Intra-Assay Reproducibility

This example illustrates the inter- and intra-assay reproducibility of a method of HPV detection of the present teachings.

In these experiments, BBI (BBI Diagnostics, West Bridgewater, Mass.) control samples with crossing point (Cp) values of 28-30, which represents a medium level of infection, were used to determine an inter- and intra-assay coefficient of variation (CV). The coefficient of variation is a statistical measure of the dispersion of data points in a data series around the mean; it represents the ratio of the standard deviation to the mean. The same specimen concentration was tested 6-10 times in a day to obtain an intra-assay CV. The same specimen concentration was tested 6-10 separate days to obtain an inter-assay CV. The Cp values were compared to determine the reproducibility of the assay. The results showed that the method of HPV detection of the present teachings was highly reproducible (FIG. 7).

Example 9

HPV Detection in Thinprep® Media

This example illustrates the diagnostic utility of the HPV method of detection of the present teachings.

Figure 8:
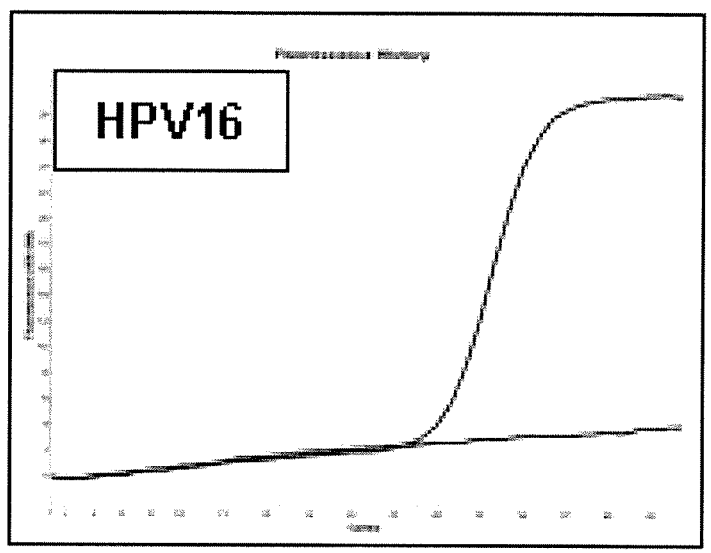
FIG. 8: Multiplex real time PCR detection of HPV16.

In these experiments, an HPV control specimen in ThinPrep® media obtained from BBI (BBI Diagnostics, West Bridgewater, Mass.) was used. The BBI control, ACCURUN 370 HPV DNA Positive Control Series 500 (BBI Diagnostics, Westbridgewater, Mass.) contained cervical cancer cell line SiHa that contained HPV16. 1000 µL of the BBI control was centrifuged to 200 µL and nucleic acid was extracted and eluted into 100 µL TE. The real time PCR amplication was performed following standard operating procedure in 4 wells, as described for the method of HPV detection in Example 2. Each of the 4 wells comprised 8 µL of the extracted nucleic acid, 2 µL of HPV A, B, C, or D mix, and 10 µL of Probesmaster. The method of HPV detection of the present teachings detected HPV 16, as shown in FIG. 8.

Example 10

Validation with Known Hpv Positive and Negative Specimens

The example demonstrates validation of the method of HPV detection of the present teachings with known positive and negative specimens.

In these experiments, 223 cervical specimens were tested using the method of HPV detection as disclosed in Example 2. Using the method of the present teachings produced 117 positives for HPV and 106 negatives for HPV, which was in 91.6% positive agreement and 92.3% negative agreement with the known specimens.

Example 11

Real Time PCR Detection Formats and Chemistries

These are examples of other real time PCR technologies that could be successfully used in the instant invention.

Detection and Quantification without Target-Specific Probes

Intercalating Dyes

DNA-binding dyes like ethidium bromide (EtBr), YO-PRO 1, SYBR Green I (FMC Bioproducts, Rockland, Me., USA) or BEBO intercalate in a non-specific manner into double-stranded DNA molecules and, in the bound state, emit fluorescence when excited by an appropriate light source. During the annealing and extension steps, an increasing amount of dye binds to the newly synthesized DNA strands leading to maximum fluorescence emission at the end of the elongation phase. As soon as the DNA is denatured again during PCR cycling, intercalated dye molecules are released into the solution resulting in a drop of fluorescence. The fluorescence is recorded after each cycle at the end of the elongation phase, and reflects the number of PCR products generated during the amplification process.

iC/iG Nucleotides

The system is based on EraGen's expanded genetic alphabet technology, consisting of 2'-deoxy-5-methyl-isocytidine (iC) and 2'-deoxy-isoguanosine (iG) nucleotide bases. These isobases pair only with each other and are efficiently incorporated during PCR. They are used to site-specifically incorporate a quencher molecule (Dabcyl) adjacent to a fluorophore. Proprietary EraGen software is used to convert fluorescence detection into a qualitative or quantitative assay result.

Detection and Quantification by Using Target-Specific Probes

Detection formats based on specific hybridization of one or two fluorescencelabelled oligonucleotide probes to the target sequence during amplification are the most frequently reported formats for virus detection in diagnostic assays. Depending on the chemistry used, different types of fluorogenic probes have been introduced.

Hydrolysis Probes

Most assays described for the detection of viral DNA or RNA are based on the use of hydrolysis probes. Hydrolysis probes (Applied Biosystems, AB, Foster City, Calif., USA), also referred to as TaqMan® or 5'-nuclease probes, are non-extendible target-specific oligonucleotide probes that bind to the target strand between the PCR primers. They are dually labelled with a fluorescent reporter dye (e.g. FAM or VIC) covalently attached to the 50-end, and a quencher dye (e.g. TAMRA), covalently attached to the 3'-end. When the reporter molecule on the TaqMan probe is stimulated by an appropriate light source to emit fluorescence, the energy is transferred to the quencher, thereby suppressing the emission of fluorescence by the reporter. This physical principle is known as the fluorescence resonance energy transfer (FRET). The transfer of energy works efficiently only across very short distances, and decreases rapidly when the reporter and quencher molecules move apart. During PCR, when the DNA polymerase extends the primers, the hybridized probes are cleaved by the 5'-exonuclease activity of the enzyme and the corresponding quencher and reporter molecules are separated. The energy transfer to the quencher molecule is thus abrogated, and the reporter starts emitting fluorescence which can be measured at the end of each extension step.

Hybridization Probes

Another detection format frequently used for the detection of DNA viruses is based on hybridization probes (HybProbe). This method relies on the use of two oligonucleotide probes that hybridize next to each other to a sequence located between the amplification primers. One of these probes is labeled with a donor dye at the 30 end (e.g. Fluorescein, emitting green light), the other is labelled with an acceptor dye at the 50 end (e.g. LC Red 640 or LC Red 705, emitting red light). The probes are designed to hybridize during the annealing step to the same strand in a head-to-tail arrangement, at a distance of 1-5 nucleotides to bring the two dyes in close proximity (hence the name "kissing" probes). The donor dye is stimulated by an appropriate light source to emit fluorescence. If both probes are bound to the specific target sequences, the fluorescence energy is transferred from the donor to the acceptor molecules (FRET), and the excited fluorophore emits a fluorescent signal, which is detected and measured at the end of each annealing step.

Molecular Beacons

A less commonly used detection format is based on molecular beacons. Molecular beacons are oligonucleotide probes containing flanking sequences of 5-7 nucleotides designed to be complementary to each other, and an intervening sequence complementary to the target of interest. The ends of the probe are labelled with a fluorescent and a non-fluorescent quenching dye (DABCYL), respectively. The term "molecular beacon" is derived from the fact that in solution the complementary sequences of the probe anneal to each other forming a stem-like structure, whereas the intervening sequence remains single-stranded and loops out. The result is a hairpin structure that brings the fluorescent dye and the quencher in close proximity, leading to efficient quenching of the fluorophore. The energy is released from the quencher dye in the form of heat (collisional quenching). In the presence of specific template, the intervening loop sequence of the molecular beacon binds to the target. This leads to a conformational transition from the hairpin structure to a linear structure, resulting in the separation of fluorophore and quencher. Energy transfer no longer occurs, and the fluorescence emitted can be detected at the end of each annealing step.

Scorpions

With Scorpion probes, sequence-specific priming and PCR product detection is achieved using a single oligonucleotide. The Scorpion probe maintains a stem-loop configuration in the unhybridized state. The fluorophore is attached to the 5' end and is quenched by a moiety coupled to the 3' end. The 3' portion of the stem also contains sequence that is complementary to the extension product of the primer. This sequence is linked to the 5' end of a specific primer via a non-amplifiable monomer. After extension of the Scorpion primer, the specific probe sequence is able to bind to its complement within the extended amplicon thus opening up the hairpin loop. This prevents the fluorescence from being quenched and a signal is observed.

Melting Curve Analysis

This approach to assessing the specificity of generated PCR products is applicable to real-time assays based on the use of intercalating dyes, hybridization probes or molecular beacons. In melting curve analysis, measurements of fluorescence are performed at the end of the PCR reaction. The temperature in the reaction tubes is gradually raised until complete denaturation of double-stranded DNA molecules occurs (TD) (TD=denaturing temperature=temperature at which the double stranded DNA amplicons are denatured). The target—probe hybrids melt at a specific melting temperature (Tm) (Tm=melting temperature (temperature at which 50% of the probe—target hybrids have dissociated)) according to their sequence, length, and GC content, thus leading to a characteristic pattern of fluorescence kinetics. The melting curve analysis is done by plotting the intensity of fluorescence against the temperature gradient on a logarithmic scale. Melting temperature profiles can be used to discriminate full length amplicons from shorter products, such as primer dimers, by their reduced TD. Moreover, non-specific PCR products displaying a different sequence can be differentiated from specific amplicons. Even single-base differences can be identified by different TM and can be exploited to identify and genotype highly homologous viruses. With appropriately validated melting curve analysis, it is also possible to determine the quantity of specific ampl icons as a basis for the calculation of initial target copy numbers.

Recent Technical Developments of Primer and Probe Modification for RQ-PCR Analysis A new generation of modified RQ-PCR probes or primers revealing increased thermal duplex stability and improved specificity for their target sequences has recently been launched by different vendors. The employment of modified oligonucleotides as primers or probes can provide more accurate target discrimination and quantification, which may be particularly useful for the detection and quantitative analysis of traditionally problematic target sequences, like GC- or AT-rich regions.

PNA-Probes

Peptide nucleic acids (PNAs) are nucleic acid analogs in which the phosphate/sugar backbone is replaced by an uncharged polyamine backbone. The side groups consist of nitrogenous purine and pyrimidine bases, identical to biological nucleic acids. The binding to complementary base sequences is stronger and more specific than that achieved with DNA or RNA probes. The greater stability is reflected by a higher TM as compared to the corresponding DNA/DNA or DNA/RNA duplexes. PNA/DNA hybridization is significantly more affected by base mismatches than DNA/DNA hybridization. A single PNA/DNA mismatch reduces the $T_m$ by an average of 15° C., compared with 11° C. in a DNA/DNA duplex. This allows shorter lengths of PNA probes to be used in situations where longer DNA probes are normally employed. However, the specificity of the probes requires careful consideration: while a 15-mer PNA probe will have roughly the same melting temperature as a standard 25-mer DNA probe, the former will not display an equally high specificity MGB™ Probes TaqMan Minor Groove Binding (MGB™) probes (Applied Biosystems, AB, Foster City, Calif., USA) are short oligonucleotides characterized by the conjugation of minor groove binders, such as dihydrocyclopyrroloindole, at the or, less commonly, at the 5'-end. This chemical modification increases the Tm of the hybridized probe and facilitates highly specific binding to the targeted sequence at the minor groove of the DNA helix. The difference in Tm-values between completely and incompletely matched probes is pronounced, thus providing a basis for reliable discrimination between sequences displaying minimal differences in the base pair composition.

LNA® Primers and Probes

The term locked nucleic acid (LNA®) describes oligonucleotide modifications characterized by the presence of one or more bicyclic ribose analogs. The structural resemblance to native nucleic acids leads to very good solubility in water and easy handling. In contrast to PNA and MGB chemistry, LNA modifications are applicable to both primers and probes in RQ-PCR assays. LNA substitutions to DNA oligonucleotides confer exceptional biological stability and significantly increased affinity to their complementary DNA targets. The increased thermal stability is dependent on the number of LNA monomers present in the sequence. LNA modifications greatly increase the melting temperature of oligonucleotides and the differences in TM between perfectly and imperfectly matched nucleic acid duplexes, thus facilitating the discrimination even between single base mutations. Owing to these properties, LNA-containing oligonucleotides used in RQ-PCR assays have a length ranging between 13 and 20 nucleotides (nt), which is significantly shorter than unmodified primers and probes displaying the same Tm. The majority of Real Time PCR related info was adapted from F. Watzinger et al./Molecular Aspects of Medicine 27 (2006) 254-298, 263), which is hereby incorporated by reference.

REFERENCES

These references are incorporated herein by reference. Applicant makes no statement, inferred or direct, regarding the status of these references as prior art and reserves the right to challenge the accuracy of any statement made in these references.

1. Walboomers J M M, Jacobs M V, Manos M M, et al. Human papillomavirus is a necessary cause of invasive cervical cancer worldwide. J Pathol 1999; 189:12-9.
2. Munoz N, Bosch F X, de Sanjosé S, et al. The causal link between human papillomavirus and invasive cervical cancer: a population-based case-control study in Colombia and Spain. Int J Cancer 1992; 52:743-9.
3. Bosch F X, Lorincz A, Munoz N, Meijer C J, Shah K V. The causal relation between human papillomavirus and cervical cancer. J Clin Pathol 2002; 55:244-65.
4. Ho G Y, Burk R D, Klein S, Kadish A S, Chang C J, Palan P, Basu J, Tachezy R, Lewis R and Romney S (1995) Peristent genital human papillomavirus infection as a risk factor for persistent cervical dysplasia. J Natl Cancer Inst 87: 1365-1371
5. Dalstein V, Riethmuller D, Pretet J L, Le Bail Carval K, Sautiere J L, Carbillet J P, Kantelip B, Schaal J P, Mougin C (2003) Persistence and load of high risk HPV are predictors for development of high-grade cervical lesions: a longitudinal French cohort study. Int J Cancer 106: 396-403
6. Franco E L, Rohan T E, Villa L L. Epidemiologic evidence and human papillomavirus infection as a necessary cause of cervical cancer. *Journal of the National Cancer Institute* 91 (6):506-511 (1999).
7. Papanicolaou G N, Traut H F. The diagnostic value of vaginal smears in carcinoma of the uterus. Am J Obstet Gynecol. 1941; 42:193-206.
8. Koss L G (1989) The papanicolauou test for cervical cancer detection. A triumph and a tragedy. *JAMA* 261: 737-743
9. Nanda K, McCrory D C, Myers E R, Bastian L A, Hasselblad V, Hickey J D, et al. Accuracy of the Papanicolaou test in screening for and follow-up of cervical cytologic abnormalities: a systematic review. Ann Intern Med 2000; 132:810-9.
10. Mahlck C, Jonsson H, Lenner P (1994) Pap smear screening and changes in cervical cancer mortality in Sweden. Int J Gynecol Obstet 44: 267-272
11. Mayrand M H, Duarte-Franco E, Rodrigues I, Walter S D, Hanley J, Ferenczy A, Ratnam S, Coutlée F, Franco E L; Canadian Cervical Cancer Screening Trial Study Group. Human papillomavirus DNA versus Papanicolaou screening tests for cervical cancer. N Engl J. Med. 2007 Oct. 18; 357(16):1579-88.
12. Munoz N, Bosch F X, de Sanjose S et al. Epidemiologic classification of human papillomavirus types associated with cervical cancer. N Engl J Med 2003; 348:518-27.
13. Van Ranst M, Kaplan J B, Burk R D. Phylogenetic classification of human papillomaviruses: correlation with clinical manifestations. J Gen Virol 1992; 73:2653-60
14. Bosch F X, Manos M M, Muñoz N, et al. Prevalence of human papillomavirus in cervical cancer: a worldwide perspective. International biological study on cervical cancer (IBSCC) study group. *Journal of the National Cancer Institute* 87(11):796-802 (1995).
15. Coulon, H., and zur Hausen, H. Molecular cloning and characterization of human papillomavirus DNA derived from a laryngeal papilloma. J. Virol., 44: 393-400, 1982.

What is claimed is:

1. A method for the detection and determination of at least a genotype of HPV present in a biological sample, said method comprising:
   a) extracting DNA from a biological sample to produce a DNA sample;
   b) forming a reaction mixture comprising the DNA sample and at least two sets of a forward primer (F) and a reverse primer (R), each set of primers being specific for a single HPV type, the at least two sets of F and R being selected from the group consisting of:
   SEQ ID NO: 1 (16F) and SEQ ID NO: 2 (16R);
   SEQ ID NO: 4 (18F) and SEQ ID NO: 5 (18R);
   SEQ ID NO: 7 (31F) and SEQ ID NO: 8 (31R);
   SEQ ID NO: 10 (33F) and SEQ ID NO: 11 (33R);
   SEQ ID NO: 13 (35F) and SEQ ID NO: 14 (35R);
   SEQ ID NO: 16 (39F) and SEQ ID NO: 17 (39R);
   SEQ ID NO: 19 (45F) and SEQ ID NO: 20 (45R);
   SEQ ID NO: 22 (51F) and SEQ ID NO: 23 (51R);
   SEQ ID NO: 25 (52F) and SEQ ID NO: 26 (52R);
   SEQ ID NO: 28 (56F) and SEQ ID NO: 29 (56R);
   SEQ ID NO: 31 (58F) and SEQ ID NO: 32 (58R);
   SEQ ID NO: 34 (59F) and SEQ ID NO: 35 (59R);
   SEQ ID NO: 37 (68F) and SEQ ID NO: 38 (68R);
   SEQ ID NO: 40 (73F) and SEQ ID NO: 41 (73R); and
   SEQ ID NO: 43 (82F) and SEQ ID NO: 44 (82R);
   c) performing a polymerase chain reaction (PCR) in the reaction mixture to form a reaction product; and
   d) detecting and genotyping a reaction product associated with an HPV type.

2. The method of claim 1, wherein the biological sample comprises a bodily fluid or a bodily tissue.

3. The method of claim 1, wherein the biological sample comprises a sample selected from the group consisting of a cervical Pap specimen, a cervical swab specimen, urine, peripheral blood and tissue.

4. The method of claim 1, wherein the DNA sample comprises DNA isolated from a male human.

5. The method of claim 1, wherein the DNA sample comprises DNA isolated from a female human.

6. The method of claim 1, wherein said reaction mixture in b) comprises at least 5 sets of primers.

7. The method of claim 1, wherein said PCR method comprises the use of a real time PCR instrument.

8. The method of claim 6, wherein 5 or more different wavelengths are used in multiplex for type-specific probe detection.

9. The method of claim 1, wherein each set of the at least two sets of primers further comprises a probe (P) specific for an HPV type, the at least two sets of F, R, and P each being selected from the group consisting of:
   SEQ ID NO: 1 (16F), SEQ ID NO: 2 (16R), and SEQ ID NO: 3 (16P);
   SEQ ID NO: 4 (18F), SEQ ID NO: 5 (18R), and SEQ ID NO: 6 (18P);
   SEQ ID NO: 7 (31F), SEQ ID NO: 8 (31R), and SEQ ID NO: 9 (31P);
   SEQ ID NO: 10 (33F), SEQ ID NO: 11 (33R), and SEQ ID NO: 12 (33P);
   SEQ ID NO: 13 (35F), SEQ ID NO: 14 (35R), and SEQ ID NO: 15 (35P);

SEQ ID NO: 16 (39F), SEQ ID NO: 17 (39R), and SEQ ID NO: 18 (39P);

SEQ ID NO: 19 (45F), SEQ ID NO: 20 (45R), and SEQ ID NO: 21 (45P);

SEQ ID NO: 22 (51F), SEQ ID NO: 23 (51R), and SEQ ID NO: 24 (51P);

SEQ ID NO: 25 (52F), SEQ ID NO: 26 (52R), and SEQ ID NO: 27 (52P);

SEQ ID NO: 28 (56F), SEQ ID NO: 29 (56R), and SEQ ID NO: 30 (56P);

SEQ ID NO: 31 (58F), SEQ ID NO: 32 (58R), and SEQ ID NO: 33 (58P);

SEQ ID NO: 34 (59F), SEQ ID NO: 35 (59R), and SEQ ID NO: 36 (59P);

SEQ ID NO: 37 (68F), SEQ ID NO: 38 (68R), and SEQ ID NO: 39 (68P);

SEQ ID NO: 40 (73F), SEQ ID NO: 41 (73R), and SEQ ID NO: 42 (73P); and

SEQ ID NO: 43 (82F), SEQ ID NO: 44 (82R), and SEQ ID NO: 45 (82P); and wherein the detecting and genotyping a reaction product associated with an HPV type comprises detecting an HPV type-specific probe in the reaction product.

10. The method of claim 1, wherein detecting the presence or absence of a reaction product associated with an HPV type comprises the use of gene chips, microarrays, probe-based hybridization, or microfluidic PCR.

11. The method of claim 1, further comprising amplification of an internal control nucleic acid.

12. The method of claim 9, further comprising amplification of an internal control nucleic acid.

13. A method for detection of HPV in a biological sample comprising:
(a) providing a DNA sample;
(b) forming at least four multiplex reaction mixtures;
a first multiplex reaction mixture comprising
(i) a forward primer consisting of SEQ ID NO: 7 (31F) and a reverse primer consisting of SEQ ID NO: 8 (31R), said primers being specific for HPV type 31;
(ii) a forward primer consisting of SEQ ID NO: 10 (33F) and a reverse primer consisting of SEQ ID NO: 11 (33R), said primers being specific for HPV type 33;
(iii) a forward primer consisting of SEQ ID NO: 13 (35F) and a reverse primer consisting of SEQ ID NO: 14 (35R), said primers being specific for HPV type 35;
(iv) a forward primer consisting of SEQ ID NO: 34 (59F) and a reverse primer consisting of SEQ ID NO: 35 (59R), said primers being specific for HPV type 59;
(v) a first portion of the DNA sample;
a second multiplex reaction mixture comprising
(i) a forward primer consisting of SEQ ID NO: 1 (16F) and a reverse primer consisting of SEQ ID NO: 2 (16R), said primers being specific for HPV type 16;
(ii) a forward primer consisting of SEQ ID NO: 4 (18F) and a reverse primer consisting of SEQ ID NO: 5 (18R), said primers being specific for HPV type 18;
(iii) a forward primer consisting of SEQ ID NO: 22 (51F) and a reverse primer consisting of SEQ ID NO: 23 (51R), said primers being specific for HPV type 51;

(iv) a forward primer consisting of SEQ ID NO: 28 (56F) and a reverse primer consisting of SEQ ID NO: 29 (56R), said primers being specific for HPV type 56;
(v) a forward primer consisting of SEQ ID NO: 43 (82F) and a reverse primer consisting of SEQ ID NO: 44 (82R), said primers being specific for HPV type 82; and
(vi) a second portion of the DNA sample;
a third multiplex reaction mixture comprising
(i) a forward primer consisting of SEQ ID NO: 1 (16F) and a reverse primer consisting of SEQ ID NO: 2 (16R), said primers being specific for HPV type 16;
(ii) a forward primer consisting of SEQ ID NO: 19 (45F) and a reverse primer consisting of SEQ ID NO: 20 (45R), said primers being specific for HPV type 45;
(iii) a forward primer consisting of SEQ ID NO: 25 (52F) and a reverse primer consisting of SEQ ID NO: 26 (52R), said primers being specific for HPV type 52;
(iv) a forward primer consisting of SEQ ID NO: 40 (73F) and a reverse primer consisting of SEQ ID NO: 41 (73R), said primers being specific for HPV type 73; and
(v) a third portion of the DNA sample; and
a fourth multiplex reaction mixture comprising
(i) a forward primer consisting of SEQ ID NO: 16 (39F) and a reverse primer consisting of SEQ ID NO: 17 (39R), said primers being specific for HPV type 39;
(ii) a forward primer consisting of SEQ ID NO: 31 (58F) and a reverse primer consisting of SEQ ID NO: 32 (58R), said primers being specific for HPV type 58;
(iii) a forward primer consisting of SEQ ID NO: 37 (68F) and a reverse primer consisting of SEQ ID NO: 38 (68R), said primers being specific for HPV type 68; and
(iv) a fourth portion of the DNA sample;
(c) performing a polymerase chain reaction (PCR) in the first multiplex reaction mixture to form a first multiplex reaction product, the second multiplex reaction mixture to form a second multiplex reaction product, the third multiplex reaction mixture to form a third multiplex reaction product, and the fourth multiplex reaction mixture to form a fourth multiplex reaction product; and
(d) detecting and genotyping a PCR product associated with HPV in each of the first multiplex reaction product, the second multiplex reaction product, the third multiplex reaction product, and the fourth multiplex reaction product.

14. The method of claim 13, wherein the PCR is real time PCR;
the first multiplex reaction mixture further comprises
(i) a probe of SEQ ID NO: 9 (31P);
(ii) a probe of SEQ ID NO: 12 (33P);
(iii) a probe of SEQ ID NO: 15 (35P); and
(iv) a probe of SEQ ID NO: 36 (59P);
the second multiplex reaction mixture further comprises
(i) a probe of SEQ ID NO: 3 (16P);
(ii) a probe of SEQ ID NO: 6 (18P);
(iii) a probe of SEQ ID NO: 24 (51P);
(iv) a probe of SEQ ID NO: 30 (56P); and
(v) a probe of SEQ ID NO: 45 (82P);

the third multiplex reaction mixture further comprises
- (i) a probe of SEQ ID NO: 3 (16P);
- (ii) a probe of SEQ ID NO: 21 (45P);
- (iii) a probe of SEQ ID NO: 27 (52P); and
- (iv) a probe of SEQ ID NO: 42 (73P);

the fourth multiplex reaction mixture further comprises
- (i) a probe of SEQ ID NO: 18 (39P);
- (ii) a probe of SEQ ID NO: 33 (58P);
- (iii) a probe of SEQ ID NO: 39 (68P); and detecting and genotyping a PCR product associated with HPV comprises detecting the presence or absence of an HPV-type-specific probe in the real time PCR.

15. The method of claim 13 wherein providing a DNA sample comprises extracting DNA from a biological sample selected from the group consisting of a cervical Pap specimen, a cervical swab specimen, a urine sample, a peripheral blood sample, and a tissue sample.

16. The method of claim 13, wherein the DNA sample comprises DNA isolated from a male human or a female human.

17. The method of claim 13, wherein the PCR is real time PCR.

18. The method of claim 17 wherein 5 or more different wavelengths are used in multiplex for type-specific probe detection.

19. The method of claim 11, wherein said internal control nucleic acid is amplified using a forward primer specific to beta-globin consisting of SEQ ID NO: 46 (BG-F) and a reverse primer specific to beta-globin consisting of SEQ ID NO: 47 (BG-R).

20. The method of claim 12, wherein said internal control nucleic acid is amplified using a forward primer specific to beta-globin consisting of SEQ ID NO: 46 (BG-F) and a reverse primer specific to beta-globin consisting of SEQ ID NO: 47 (BG-R).

* * * * *